US010064813B2

(12) United States Patent
Florence et al.

(10) Patent No.: US 10,064,813 B2
(45) Date of Patent: *Sep. 4, 2018

(54) COSMETIC COMPOSITIONS

(71) Applicant: Mary Kay Inc., Addison, TX (US)

(72) Inventors: Tiffany Florence, Addison, TX (US);
Michelle Hines, Addison, TX (US);
David Gan, Addison, TX (US)

(73) Assignee: Mary Kay Inc., Addison, TX (US)

( * ) Notice: Subject to any disclaimer, the term of this patent is extended or adjusted under 35 U.S.C. 154(b) by 13 days.

This patent is subject to a terminal disclaimer.

(21) Appl. No.: 14/963,886

(22) Filed: Dec. 9, 2015

(65) Prior Publication Data

US 2016/0095814 A1 Apr. 7, 2016

Related U.S. Application Data

(63) Continuation of application No. 13/468,874, filed on May 10, 2012, now Pat. No. 9,233,062.

(60) Provisional application No. 61/550,813, filed on Oct. 24, 2011, provisional application No. 61/495,208, filed on Jun. 9, 2011, provisional application No. 61/484,542, filed on May 10, 2011.

(51) Int. Cl.

| | | |
|---|---|---|
| *A61K 8/97* | (2017.01) | |
| *A61K 8/41* | (2006.01) | |
| *A61K 8/70* | (2006.01) | |
| *A61K 8/06* | (2006.01) | |
| *A61K 8/11* | (2006.01) | |
| *A61K 8/34* | (2006.01) | |
| *A61K 8/73* | (2006.01) | |
| *A61K 8/60* | (2006.01) | |
| *A61K 8/43* | (2006.01) | |
| *A61K 8/42* | (2006.01) | |
| *A61K 8/37* | (2006.01) | |
| *A61K 8/20* | (2006.01) | |
| *A61Q 17/04* | (2006.01) | |
| *A61Q 19/00* | (2006.01) | |
| *A61Q 19/10* | (2006.01) | |
| *A61Q 19/02* | (2006.01) | |
| *A61Q 19/08* | (2006.01) | |
| *A61K 8/64* | (2006.01) | |

(52) U.S. Cl.
CPC ............... *A61K 8/97* (2013.01); *A61K 8/064* (2013.01); *A61K 8/11* (2013.01); *A61K 8/20* (2013.01); *A61K 8/34* (2013.01); *A61K 8/342* (2013.01); *A61K 8/345* (2013.01); *A61K 8/347* (2013.01); *A61K 8/37* (2013.01); *A61K 8/375* (2013.01); *A61K 8/41* (2013.01); *A61K 8/42* (2013.01); *A61K 8/43* (2013.01); *A61K 8/60* (2013.01); *A61K 8/64* (2013.01); *A61K 8/70* (2013.01); *A61K 8/73* (2013.01); *A61K 8/733* (2013.01); *A61Q 17/04* (2013.01); *A61Q 19/007* (2013.01); *A61Q 19/008* (2013.01);

*A61Q 19/02* (2013.01); *A61Q 19/08* (2013.01); *A61Q 19/10* (2013.01); *A61K 2800/522* (2013.01); *A61K 2800/596* (2013.01); *A61K 2800/70* (2013.01); *A61K 2800/78* (2013.01); *A61K 2800/782* (2013.01)

(58) Field of Classification Search
None
See application file for complete search history.

(56) References Cited

U.S. PATENT DOCUMENTS

| | | | |
|---|---|---|---|
| 4,699,778 A | 10/1987 | Marty | 424/59 |
| 6,492,326 B1 | 12/2002 | Robinson et al. | 514/18.6 |
| 6,927,205 B2 | 8/2005 | Patt | 514/18.7 |
| 6,927,206 B2 | 8/2005 | Patt | 514/2.4 |
| 6,998,129 B2 | 2/2006 | Breton et al. | 424/401 |
| 7,128,923 B2 | 10/2006 | Patt | 424/400 |
| 7,863,417 B2 | 1/2011 | Ziegler et al. | 530/331 |
| 2002/0192246 A1* | 12/2002 | Jensen | A61K 8/97 424/401 |
| 2006/0018867 A1 | 1/2006 | Kawakaki et al. | 424/70 |
| 2006/0233738 A1* | 10/2006 | Miyata | A61K 8/97 424/74 |
| 2006/0257386 A1* | 11/2006 | Zimmerman | A61K 8/66 424/94.6 |
| 2007/0184012 A1 | 8/2007 | Perrier et al. | 424/74 |

(Continued)

FOREIGN PATENT DOCUMENTS

| | | |
|---|---|---|
| EP | 2319914 | 5/2011 |
| WO | WO 2009/071213 | 6/2009 |

(Continued)

OTHER PUBLICATIONS

International Cosmetic Ingredient Dictionary Handbook, 12$^{th}$ edition, vol. 1, pp. 458-460 (2008).
International Cosmetic Ingredient Dictionary Handbook, 12$^{th}$ edition, vol. 2, pp. 2452-2453 (2008).
International Cosmetic Ingredient Dictionary Handbook, 12$^{th}$ edition, vol. 2, pp. 2633-2634 (2008).
International Cosmetic Ingredient Dictionary Handbook, 12$^{th}$ edition, vol. 2, p. 2042 (2008).
International Cosmetic Ingredient Dictionary Handbook, 12$^{th}$ edition, vol. 1, p. 116 (2008).

(Continued)

*Primary Examiner* — Taeyoon Kim
*Assistant Examiner* — Srikanth Patury
(74) *Attorney, Agent, or Firm* — Norton Rose Fulbright US LLP

(57) ABSTRACT

Disclosed are compositions and methods for their use that can be used in cosmetic applications. The composition can include an effective amount of a *Centella asiatica* stem cells to reduce the activity of hyaluronidase in skin, an effective amount of tetradecyl aminobutyroylvalylamino butyric urea trifluoroacetate or *Alpinia galanga* leaf extract to promote the production of hyaluronic acid in skin, an effective amount of tripeptide-1 to promote the production of fibronectin and laminin in skin, and a dermatologically acceptable vehicle.

16 Claims, 1 Drawing Sheet

(56) References Cited

U.S. PATENT DOCUMENTS

| | | | | |
|---|---|---|---|---|
| 2008/0305059 | A1* | 12/2008 | Chaudhuri | A61K 8/347 424/62 |
| 2009/0036402 | A1 | 2/2009 | Sene et al. | 514/54 |
| 2009/0169652 | A1 | 7/2009 | Osborne | 424/727 |
| 2009/0234382 | A1* | 9/2009 | Dillon | A61K 8/0208 606/204.35 |
| 2010/0021401 | A1 | 1/2010 | Sallander | 424/59 |
| 2010/0028317 | A1* | 2/2010 | Maes | A61K 8/347 424/94.1 |
| 2010/0086573 | A1* | 4/2010 | Anderson | A61K 8/14 424/401 |
| 2010/0190742 | A1* | 7/2010 | Breton | A61K 8/02 514/54 |
| 2010/0233128 | A1 | 9/2010 | Panasenko | 242/93.4 |
| 2010/0247563 | A1* | 9/2010 | Hines | A61K 8/97 424/195.16 |
| 2011/0008394 | A1* | 1/2011 | Bechetoille | A61K 8/97 424/278.1 |
| 2011/0229431 | A1 | 9/2011 | Kurfurst et al. | 424/74 |
| 2011/0294876 | A1* | 12/2011 | Kuper | A23G 3/36 514/465 |
| 2011/0305735 | A1* | 12/2011 | Cebrian Puche | A61K 8/64 424/401 |
| 2012/0064182 | A1* | 3/2012 | Gohla | A61K 8/64 424/728 |
| 2012/0121737 | A1* | 5/2012 | Vielhaber | A23C 9/1307 424/737 |

FOREIGN PATENT DOCUMENTS

| | | |
|---|---|---|
| WO | WO 2009/127058 | 10/2009 |
| WO | WO 2010/004099 | 1/2010 |
| WO | WO 2010/067212 | 6/2010 |
| WO | WO 2010/106044 | 9/2010 |

OTHER PUBLICATIONS

International Cosmetic Ingredient Dictionary Handbook, 12$^{th}$ edition, vol. 1, p. 198 (2008).
International Cosmetic Ingredient Dictionary Handbook, 12$^{th}$ edition, vol. 1, p. 214 (2008).
International Cosmetic Ingredient Dictionary Handbook, 12$^{th}$ edition, vol. 2, p. 2399 (2008).
International Cosmetic Ingredient Dictionary Handbook, 12$^{th}$ edition, vol. 2, pp. 1499-1450 (2008).
International Cosmetic Ingredient Dictionary Handbook, 12$^{th}$ edition, vol. 1, p. 314 (2008).
International Cosmetic Ingredient Dictionary Handbook, 12$^{th}$ edition, vol. 1, p. 610 (2008).
International Cosmetic Ingredient Dictionary Handbook, 12$^{th}$ edition, vol. 1, p. 1146 (2008).
International Cosmetic Ingredient Dictionary Handbook, 12$^{th}$ edition, vol. 2, p. 1767 (2008).
International Cosmetic Ingredient Dictionary Handbook, 12$^{th}$ edition, vol. 1, p. 855 (2008).
International Cosmetic Ingredient Dictionary Handbook, 12$^{th}$ edition, vol. 2, p. 2478 (2008).
International Cosmetic Ingredient Dictionary Handbook, 12$^{th}$ edition, vol. 1, p. 331 (2008).
International Cosmetic Ingredient Dictionary Handbook, 12$^{th}$ edition, vol. 1, p. 1158 (2008).
International Cosmetic Ingredient Dictionary Handbook, 12$^{th}$ edition, vol. 2, p. 2363 (2008).
International Cosmetic Ingredient Dictionary Handbook, 12$^{th}$ edition, vol. 2, pp. 2315-2317 (2008).
International Cosmetic Ingredient Dictionary Handbook, 12$^{th}$ edition, vol. 1, pp. 650 (2008).
International Cosmetic Ingredient Dictionary Handbook, 12$^{th}$ edition, vol. 1, p. 584 (2008).
International Cosmetic Ingredient Dictionary Handbook, 12$^{th}$ edition, vol. 1, pp. 1100-1101 (2008).
International Cosmetic Ingredient Dictionary Handbook, 12$^{th}$ edition, vol. 1, pp. 212-213 (2008).
International Cosmetic Ingredient Dictionary Handbook, 12$^{th}$ edition, vol. 2, p. 1731 (2008).
International Cosmetic Ingredient Dictionary Handbook, 12$^{th}$ edition, vol. 1, p. 60 (2008).
International Search Report and Written Opinion issued in PCT Application No. PCT/US2012/037308, dated Nov. 26, 2012.
Database GNPD [Online] MINTEL; Aug. 2010 (Aug. 2010), "Sleep Mask" Database Accession No. 1381282.
Database GNPD [Online] MINTEL; Dec. 2010 (Dec. 2012), "Stimulant II Corrective Serum" Database Accession No. 1469715.
Database GNPD [Online] MINTEL; Mar. 2011 (Mar. 2011), "Biodynamic Lifting Neck Cream" Database Accession No. 1589488.
Database GNPD [Online] MINTEL; May 2008 (May 2008), "Hypnotic Eye Potion" Database Accession No. 912250.
Supplementary European Search Report dated Dec. 2, 2014 in European Application No. 12782287.
"Acceleration of Skim Compacting and Remodeling with Novel Peptide" Cosmetics and Personal Care 2:6-9, 2011. (English translation of abstract).
Office Action dated Dec. 22, 2014 in Chinese Application No. 201280000499.5
CentellaStems, Centella Asiatica Stem GTM, IRB Product Sheet, 2015.
Alban-Muller-Catalog, Product Catalog, 2014.
Centella-INCI, Centella Asiatica Meristem Cell Culture, INCI Database Entry, Mar. 17, 2010.
Xanthan-Gum, INCI Database Entry, Feb. 16, 2009.
Centella, Centella Asiatica Stem Cells, Product Sheet, Resources, of Nature Inc., Oct. 19, 2010.
Centella Asiatica Stem G, IRB, Product data sheet, Aug. 2011.
SYN-Hycan, Pentapharm product sheet, May 10, 2009.
Kollaren, Dermis enhancer, product sheet, Atrium innovations, Sep. 2006.
Jaboticabas, Web page, Jaboticaba taxonomy, Apr. 15, 2009.
Ronacare Luremin, EMD product data sheet, May 20, 2013, web page.
Luremin Trademark filing, USPTO trademark page, Jun. 1, 2010.

* cited by examiner

COSMETIC COMPOSITIONS

CROSS REFERENCE TO RELATED APPLICATIONS

This application is a continuation of U.S. application Ser. No. 13/468,874, filed May 10, 2012, which claims the benefit of U.S. Provisional Application No. 61/550,813, filed Oct. 24, 2011, U.S. Provisional Application No. 61/495,208, filed Jun. 9, 2011, and U.S. Provisional Application No. 61/484,542, filed May 10, 2011. The contents of all of the referenced applications are incorporated into this application by reference.

BACKGROUND OF THE INVENTION

A. Field of the Invention

The present invention relates generally to a combination of ingredients that can reduce the appearance of deep lines and wrinkles, restore lifted contours, and recapture a youthful volume in the skin. In particular, the following combinations were found to work well with one another to treat skin in such a manner and to ultimately provide for a more youthful appearance of skin: Combination 1: (1) *Centella asiatica* stem cells, which can reduce the activity of hyaluronidase in skin; (2) tetradecyl aminobutyroylvalylamino butyric urea trifluoroacetate, which can promote the production of hyaluronic acid in skin; and (3) tripeptide-1, which can promote the synthesis of fibronectin and laminin in skin; Combination 2: (1) *Centella asiatica* stem cells, which can reduce the activity of hyaluronidase in skin; (2) *Alpinia galanga* leaf extract, which can promote the production of hyaluronic acid in skin; and (3) tripeptide-1, which can promote the production of fibronectin and laminin in skin; and Combination 3: (1) *Centella asiatica* stem cells, which can reduce the activity of hyaluronidase in skin; and (2) tripeptide-1, which can promote the synthesis of fibronectin and laminin in skin.

B. Description of Related Art

Many factors contribute to skin aging such as the actual age of a person, the amount of exposure to environmental factors (e.g., sun light, pollution, chemicals, smoke, etc.), and how well a person has taken care of their skin. In particular, skin aging concerns two processes—intrinsic aging, which is related to the natural aging process and genetic influences, and extrinsic, or accumulated damage due to environmental factors such as sun exposure. This combination of factors eventually leads to visible signs of aging, and over time these signs progress through three stages—early, moderate and advanced.

The early signs of skin aging include the first stages of visible fine lines, especially around the eyes, and the beginning of uneven skin tone. Cell turnover begins to slow, and this can have a dulling effect on the complexion. Collagen and elastin—while still healthy—can start to suffer early damage, leaving skin slightly less resilient. If the matrix is left unprotected, wrinkles that are forming underneath the surface of the skin will eventually become more noticeable due to damage in the dermal layer. Eyes can occasionally look puffy, and pores appear slightly more noticeable. Typically, this occurs in an age range of about 25 to 35 years of age.

The moderate signs of skin aging include more pronounced expression lines around the eyes, the mouth and on the forehead. Underneath the eyes dark circles can become more noticeable. The skin's support structure becomes weaker as less collagen is produced, and elastin fibers begin to lose their ability to "snap" back. Skin loses vital moisture more easily, and dark spots can become more of an issue. Fine lines on the neck can become more visible, and "marionette" lines on either side of the mouth can begin to appear. More significant age spots begin to surface, eyes may look tired more often, and pores appear larger. This typically occurs in an age range of about 35 to 50 years of age.

The advanced signs of skin aging include "static" deep lines and wrinkles that are visible even when the face is at rest. The supporting structure of collagen and elastin is severely compromised and skin sagging, especially in the cheek and jawline areas, becomes evident. The neck shows signs of cumulative damage, with the skin becoming loose and marked by horizontal wrinkles called "tree rings." Dark spots become more prominent, and the eye area can show noticeable crepiness, sagging, puffiness and more pronounced dark circles in addition to a "drooping" upper eyelid. Skin loses its youthful volume and lift due to a loss of natural cushioning, and skin dryness is more pronounced as the external barrier is compromised, oil production slows and internal moisture levels drop. Cell turnover slows dramatically, and dead skin cells remain on the skin's surface which can dull the complexion and make pores more noticeable. The thickness of the skin is also impacted, and as it becomes thinner it's more easily irritated. Typically this occurs in an age range of above 50 years of age.

Current products on the market either do not effectively address ageing skin or have skin irritating effects. The inventors, however, have discovered a unique combination of ingredients that work in a symbiotic relationship with one another to effectively address the signs of early, moderate, and advanced skin ageing.

SUMMARY OF THE INVENTION

The inventors have discovered that particular combinations of ingredients can be used revitalize and rebuild the skin matrix by attacking and up regulating various biochemical pathways. These pathways include reducing the activity of hyaluronidase in skin, promoting the production of hyaluronic acid in skin; and promoting the synthesis of fibronectin and laminin in skin.

In one instance, there is disclosed a topical skin composition comprising an effective amount of a *Centella asiatica* stem cells to reduce the activity of hyaluronidase in skin, an effective amount of tetradecyl aminobutyroylvalylamino butyric urea trifluoroacetate or *Alpinia galanga* leaf extract to promote the production of hyaluronic acid in skin, an effective amount of tripeptide-1 to promote the production of fibronectin and laminin in skin, and a dermatologically acceptable vehicle. The topical skin composition can include an effective amount of tetradecyl aminobutyroylvalylamino butyric urea trifluoroacetate to promote the production of hyaluronic acid in skin. The topical skin composition can include an effective amount of *Alpinia galanga* leaf extract to promote the production of hyaluronic acid in skin. The *Centella asiatica* stem cells can be a mixture of *Centella asiatica* stem cells, glycerin, and xanthan gum. The tetradecyl aminobutyroylvalylamino butyric urea trifluoroacetate can be a mixture of tetradecyl aminobutyroylvalylamino butyric urea trifluoroacetate, magnesium chloride, glycerin, and water. The *Alpinia galanga* leaf extract can be a mixture of water, butylene glycol, *Alpinia galanga* leaf extract, xanthan gum, and caprylic/capric triglyceride. The tripeptide-1 can be a mixture of tripeptide-1, water, urea, glucose, and guanidine HCL. The composition can include 0.000001 to 10% by weight of *Centella asiatica* stem cells, 0.000001 to 10% by weight of tetradecyl aminobutyroylvalylamino butyric urea trifluoroacetate or *Alpinia galanga* leaf extract, and 0.000001 to 10% by weight of tripeptide-1. In particular aspects, the amount of said ingredients can be as low as 0.000001 and as high as 1%, and more so as low as 0.01 to as high as 0.5% by weight. As explained elsewhere, the composition can be formulated in a wide variety of types, non-limiting examples of which are serums, creams, lotions, cleansers, and the like. In some instances, the compositions can further include any one of, any combination of, or all of *Myrciaria jaboticaba* extract, *Secale cereale* seed extract, *Spilanthes acmella* flower extract, *Pisum sativum* extract, *Alteromonas* ferment filtrate or extract, and dihydroxymethyl chromone. In other instances, the compositions can further include any one of, any combination of, or all of *Secale cereale* seed extract, *Alteromonas* ferment filtrate or extract, *Myrciaria jaboticaba* extract, *Argania spinosa* kernel extract, *Asparagopsis armata* extract, *Ascophyllum nodosum* extract, and *Rubus fruticosus* leaf extract. In yet other instances, the compositions can further include any one of, any combination of, or all of *Magnolia officinalis* bark extract or *Magnolia grandiflora* bark extract, *Magnolia biondii* bud/flower extract, *Brassica campestris* sterols, *Citrus grandis* peel extract, Caprooyl tetrapeptide-3, *Pisum Sativum* extract, Hesperidin methyl chalcone, and Palmitoyl tetrapeptide-7. In even further instances, the compositions can also include any one of, any combination of, or all of *Silybum marianum* extract or silymarin, 4-t-Butylcyclohexanol, Hexylresorcinol, and *Cestrum latifolium* extract. The compositions can further include any one of, any combination of, or all of retinol, *Punica granatum* extract or sterols thereof, *Codium tomentosum* extract, *Cinnamomum Cassia* bark extract, and *Glycyrrhiza glabra* (Licorice) root extract. In even other aspects, the compositions can further include a mixture of maltodextrin, lipase, and subtilisin. In other aspects, the compositions can further include any one of, any combination of, or all of *Secale cereale* seed extract, *alteromonas* ferment filtrate or extract, *Codium tomentosum* extract, *Argania spinosa* kernel extract, *Asparagopsis armata* extract, *Ascophyllum nodosum* extract, and *Rubus fruticosus* leaf extract. The compositions can further include any one of, any combination of, or all of *Magnolia officinalis* bark extract or *Magnolia grandiflora* bark extract, *Magnolia biondii* bud/flower extract, hesperidin methyl calcone, *Pisum sativum* extract, *Brassica campostris* sterols, *Citrus grandis* peel extract, dipeptide-2, palmitoyl tetrapeptide-7, and ascorbyl tetraisopalmitate. The compositions can also include any one of, any combination of, or all of retinol, *Punica granatum* extract or sterols thereof, *Codium tomentosum* extract, adenosine, *Cinnamomum cassia* bark extract, adenosine, and *Glycyrrhiza glabra* root extract. Also contemplated is a method for treating skin comprising topically applying any one of said compositions to skin in need of treatment, wherein topical application of the composition reduces the activity of hyaluronidase in skin, increases the production of hyaluronic acid in skin, and increases the production of fibronectin and/or laminin in skin. As explained elsewhere, the pathways that the combination of ingredients affect allow it to treat a wide range of skin conditions, non-limiting examples of which include fine line or wrinkle, skin that has reduced elasticity, loose skin, skin that is deficient in hyaluronic acid production and skin that is deficient in matrix protein production (e.g., fibronectin, laminin, collagen I, collagen III, and/or elastin). In particular instances, the compositions can be applied to the periorbital area of a person's skin (which is the area adjacent to and around the eyes). The compositions can be applied to facial skin, neck skin, shoulder skin, arms, legs, hands, and back skin. Also explained elsewhere, the compositions can be formulated as a leave-on product or a rinse of product. In some instances, the compositions remain on the skin for at least 5, 10, 30, or 60 minutes after topical application, or at least 12 hours after topical application or at least 24 hours after topical application.

In one instance, there is disclosed a topical skin and method for its use that includes a dermatologically acceptable vehicle and at least one, two or all three of the following: an effective amount of a *Centella asiatica* stem cells to reduce the activity of hyaluronidase in skin; an effective amount of tetradecyl aminobutyroylvalylamino butyric urea trifluoroacetate or *Alpinia galanga* leaf extract to promote the production of hyaluronic acid in skin; and an effective amount of tripeptide-1 to promote the production of fibronectin and laminin in skin.

Another aspect of the present invention includes a combination of *Centella asiatica* extract or *Centella asiatica* meristem cell culture, tetradecyl aminobutyroylvalylamino butyric urea trifluoroacetate, and tripeptide-1, have the ability to increase synthesis of extracellular matrix proteins (e.g., collagen, elastin, and hyaluronic acid) and proteins localized in the dermal-epidermal junction (e.g., laminin and fibronectin) of the skin. This combination can be placed into a composition, which can be formulated as a cream, lotion, emulsion, serum, or cleanser, for instance.

In another instance, the inventors have discovered that a combination of *Centella asiatica* extract or *Centella asiatica* meristem cell culture, tetradecyl aminobutyroylvalylamino butyric urea trifluoroacetate, tripeptide-1, *Myrciaria jaboticaba* extract, *Secale cereale* seed extract, *Spilanthes acmella* flower extract, *Pisum sativum* extract, *Alteromonas* ferment filtrate or extract, and dihydroxymethyl chromone in a composition can also increase synthesis of extracellular matrix proteins (e.g., collagen, elastin, and hyaluronic acid) and proteins localized in the dermal-epidermal junction (e.g., laminin and fibronectin) of the skin and provide additional skin benefits. In particular aspects, this combination of ingredients has been found to work well with skin located on the neck and face. In certain embodiments, a composition having this combination of ingredients is formulated as a serum.

In still another embodiment, the inventors have discovered that a combination of *Centella asiatica* extract or *Centella asiatica* meristem cell culture, tetradecyl aminobutyroylvalylamino butyric urea trifluoroacetate, tripeptide-1, *Secale cereale* seed extract, *Alteromonas* ferment filtrate or extract, *Myrciaria jaboticaba* extract, *Argania spinosa* kernel extract, *Asparagopsis armata* extract, *Ascophyllum nodosum* extract, and *Rubus fruticosus* leaf extract can also increase synthesis of extracellular matrix proteins (e.g., collagen, elastin, and hyaluronic acid) and proteins localized in the dermal-epidermal junction (e.g., laminin and fibronectin) of the skin and provide additional skin benefits. In particular aspects, this combination of ingredients has also been found to work well with skin located on the neck and face. In certain embodiments, a composition having this combination of ingredients is formulated as a serum.

In yet another embodiment, the inventors have discovered that a combination of *Centella asiatica* extract or *Centella asiatica* meristem cell culture, *Magnolia officinalis* bark extract or *Magnolia grandiflora* bark extract, *Magnolia biondii* bud/flower extract, *Brassica campestris* sterols, *Citrus grandis* peel extract, Caprooyl tetrapeptide-3, *Pisum Sativum* extract, Hesperidin methyl chalcone, and Palmitoyl tetrapeptide-7 can also increase synthesis of extracellular matrix proteins (e.g., collagen, elastin, and hyaluronic acid) and proteins localized in the dermal-epidermal junction (e.g., laminin and fibronectin) of the skin and provide additional skin benefits. In particular aspects, this combination of ingredients has also been found to work well with skin located in the periorbital region of the face (e.g., skin around and under the eyes). In certain aspects, this combination can reduce the appearance of dark circles under the eye, puffy skin under the eye, sagging or "bags" under the eye, and increase blood circulation under the eye. In certain embodiments, a composition having this combination of ingredients is formulated as a cream or lotion or emulsion.

In still a further embodiment, the inventors have discovered that a combination of Centella asiatica extract and/or Centella asiatica meristem cell culture, Magnolia officinalis bark extract or Magnolia grandiflora bark extract, Magnolia biondii bud/flower extract; Hesperidin methyl chalcone, Pisum sativum extract, Citrus grandis peel extract, Dipeptide-2, Palmitoyl tetrapeptide-7, and Caprooyl tetrapeptide-3 can also increase synthesis of extracellular matrix proteins (e.g., collagen, elastin, and hyaluronic acid) and proteins localized in the dermal-epidermal junction (e.g., laminin and fibronectin) of the skin and provide additional skin benefits. In particular aspects, this combination of ingredients has also been found to work well with skin located in the periorbital region of the face (e.g., skin around and under the eyes). In certain aspects, this combination can reduce the appearance of dark circles under the eye, puffy skin under the eye, sagging or "bags" under the eye, and increase blood circulation under the eye. In certain embodiments, a composition having this combination of ingredients is formulated as a cream or lotion or emulsion.

In yet another embodiment, the inventors have discovered that a combination of tripeptide-1, tetradecyl aminobutyroylvalylamino butyric urea trifluoroacetate, Centella asiatica extract or Centella asiatica meristem cell culture, Silybum marianum extract or silymarin, 4-t-Butylcyclohexanol, Hexylresorcinol, and Cestrum latifolium extract can also increase synthesis of extracellular matrix proteins (e.g., collagen, elastin, and hyaluronic acid) and proteins localized in the dermal-epidermal junction (e.g., laminin and fibronectin) of the skin and provide additional skin benefits. In certain embodiments, a composition having this combination of ingredients is formulated as a cream or lotion or emulsion. In some instances, the composition can further include Ascophyllum nodosum extract and/or Asparagopsis armata extract.

In yet another embodiment, the inventors have discovered that a combination of retinol, Punica granatum extract or sterols thereof, Codium tomentosum extract, Cinnamomum Cassia bark extract, Glycyrrhiza glabra (Licorice) root extract, Centella asiatica extract or Centella asiatica meristem cell culture, and Tetradecyl aminobutyroylvalylaminobutyric urea trifluoroacetate can also increase synthesis of extracellular matrix proteins (e.g., collagen, elastin, and hyaluronic acid) and proteins localized in the dermal-epidermal junction (e.g., laminin and fibronectin) of the skin and provide additional skin benefits. In certain embodiments, a composition having this combination of ingredients is formulated as a cream or lotion or emulsion.

In still another embodiment, the inventors have discovered that a combination of Zymo Clear™ MD (mixture of maltodextrin, lipase, and subtilisin), tripeptide-1, Tetradecyl aminobutyroylvalylaminobutyric urea trifluoroacetate, and Centella Asiatica extract or Centella asiatica meristem cell culture works particularly well in a skin-cleansing base composition. Such a composition can include emulsifiers and/or surfactants but does not require emulsifiers and/or surfactants.

The inventors have also discovered that a combination of Centella asiatica extract or Centella asiatica meristem cell culture, Alpinia galanga leaf extract, and tripeptide-1, have the ability to increase synthesis of extracellular matrix proteins (e.g., collagen, elastin, and hyaluronic acid) and proteins localized in the dermal-epidermal junction (e.g., laminin and fibronectin) of the skin. This combination can be included in a topical skin composition (e.g., cream, lotion, serum, gel, etc.). A person can be identified as having decreased synthesis of extracellular matrix proteins and/or proteins localized in the dermal-epidermal junction of the skin when compared with skin that has normal synthesis of extracellular matrix proteins and/or proteins localized in the dermal-epidermal junction of the skin. The composition can be used to strengthen the dermal-epidermal junction in sagging, non-elastic, loose, or wrinkled skin.

In another aspect, the inventors have discovered that a combination of Centella asiatica extract or Centella asiatica meristem cell culture, Alpinia galanga leaf extract, tripeptide-1, Secale cereale seed extract, Alteromonas ferment filtrate or extract, Codium tomentosum extract, Argania spinosa kernel extract, Asparagopsis armata extract, Ascophyllum nodosum extract, and Rubus fruticosus leaf extract can be used to increases synthesis of extracellular matrix proteins and/or proteins localized in the dermal-epidermal junction of the skin. This combination can be included in a topical skin composition (e.g., cream, lotion, serum, gel, etc.). A person can be identified as having decreased synthesis of extracellular matrix proteins and/or proteins localized in the dermal-epidermal junction of the skin when compared with skin that has normal synthesis of extracellular matrix proteins and/or proteins localized in the dermal-epidermal junction of the skin. The composition can strengthen the dermal-epidermal junction in sagging, non-elastic, loose, or wrinkled skin. This combination works especially well on facial and neck skin.

Also disclosed is a combination of Magnolia officinalis bark extract or Magnolia grandiflora bark extract, Magnolia biondii bud/flower extract, hesperidin methyl calcone, Pisum sativum extract, Brassica campostris sterols, Citrus grandis peel extract, dipeptide-2, palmitoyl tetrapeptide-7, ascorbyl tetraisopalmitate, Centella asiatica extract or Centella asiatica meristem cell culture, and tripeptide-1. In certain aspects, the combination can further include Opuntia tuna fruit extract. This combination can be included in a topical skin composition (e.g., cream, lotion, serum, gel, etc.). This combination can be used to treat skin in the periorbital region of the face. In particular aspects, the combination can be applied to wrinkles around the eyes, crow feet, bags under the eyes, dark circles under the eye, or skin under the eye. The combination can increase blood circulation in the skin when compared with untreated skin.

In a further embodiment, there is disclosed a combination of retinol, Punica granatum extract or sterols thereof, Codium tomentosum extract, adenosine, Cinnamomum cassia bark extract, adenosine, Glycyrrhiza glabra root extract, Centella asiatica extract or Centella asiatica meristem cell culture, tripeptide-1, and Alpinia galanga leaf extract, which can be used to treat skin. This combination can be included in a topical skin composition (e.g., cream, lotion, serum, gel, etc.). The combination can be used to increase synthesis of extracellular matrix proteins and/or proteins localized in the dermal-epidermal junction of the skin. A person can be identified as having decreased synthesis of extracellular matrix proteins and/or proteins localized in the dermal-epidermal junction of the skin when compared with skin that has normal synthesis of extracellular matrix proteins and/or proteins localized in the dermal-epidermal junction of the skin. The combination can strengthen the dermal-epidermal junction in sagging, non-elastic, loose, or wrinkled skin. In particular aspects, this combination has been found to work best on facial or neck skin.

In still a further aspect, there is disclosed a topical skin composition that includes any one of, any combination of, or all of *Centella asiatica* extract or *Centella asiatica* meristem cell culture, tetradecyl aminobutyroylvalylamino butyric urea trifluoroacetate, tripeptide-1, and/or *Alpinia galanga* leaf extract. Also disclosed is a method of treating a wide variety of skin conditions with compositions have any one of, any combination of, or all of *Centella asiatica* extract or *Centella asiatica* meristem cell culture, tetradecyl aminobutyroylvalylamino butyric urea trifluoroacetate, tripeptide-1, and/or *Alpinia galanga* leaf extract.

The aforementioned combination of ingredients can be used in a wide range of applications to treat or prevent a skin condition. For instance, compositions having any of the combinations can be topically applied to skin in need of such treatment (e.g., aged skin, sun damaged skin, dry skin, dirty or oily skin, flaky skin, fine lines or wrinkles, pits or nodules, erythemic skin, sagging skin, skin that produces a reduced amount of collagen, elastin, and/or hyaluronic acid, skin that produces a reduced amount of laminin and/or fibronectin, skin having a deficient or defective dermal-epidermal junction, etc.), wherein topically application of an effective amount of said combinations can treat or prevent said skin condition. The effective amount of any one of the extracts individually or in combination can be 0.0001 to 20% by weight (or 1, 2, 3, 4, 5, 6, 7, 8, 9, 10, 20, 30, 40, or 50%). Additional skin conditions that can be treated or prevented with any one of the methods and/or compositions of the present can be: chapped skin, pruritus, spider veins, lentigo, age spots, senile purpura, keratosis, melasma, blotches, dermatitis (including, but not limited to seborrheic dermatitis, nummular dermatitis, contact dermatitis, atopic dermatitis, exfoliative dermatitis, perioral dermatitis, and stasis dermatitis), psoriasis, folliculitis, rosacea, acne, impetigo, erysipelas, erythrasma, eczema, sun burns, burned skin, open wounds, and/or skin-inflammatory skin conditions.

In one particular aspect there is disclosed a method of treating or preventing a fine line or wrinkle comprising topically applying to skin in need thereof any one of the compositions of the present invention, wherein topical application of said composition to a fine line or wrinkle treats said fine line or wrinkle.

In yet another embodiment there is disclosed a method of treating or preventing erythemic skin or symptoms associated with erythemic skin (e.g., red skin, flushed skin, etc.) comprising topically applying to skin in need thereof any one of the compositions of the present invention, wherein topical application of said composition to erythemic skin treats said erythemic skin. Erythema can be caused by skin irritation, an inflammatory response, skin sunburn, electrical treatments of skin, skin burns, contact allergies, systemic allergies, skin toxicity, exercise, insect stings, bacterial infection, viral infection, fungal infection, protozoa infection, massage, windburn, and other factors that can cause reddening or flushing of the skin etc. The compositions disclosed above and throughout this specification can be used. The compositions can also be used to reducing pain associated with erythema, sensitive skin, or inflamed skin, comprising topically applying to erythemic, sensitive, or inflamed skin a composition comprising jaboticaba fruit pulp and/or cashew fruit pulp or extracts thereof.

Also disclosed is a method of tightening or toning skin comprising topically applying to skin in need thereof a composition comprising any one of the compositions of the present invention, wherein topical application of said composition to skin tightens or tones said skin. The compositions disclosed above and throughout this specification can be used.

Also disclosed is a method of increasing the integrity of the dermal-epidermal junction ("DEJ") comprising topically applying any one of the combination of ingredients or compositions having said combinations disclosed throughout this specification to skin. This method can stimulate the production of proteins and enzymes in dermal and epidermal cells that aid in connecting the dermal layer to the epidermal layer. Not wishing to be bound by theory, it is believed that the combination of ingredients disclosed throughout the specification (e.g., *Centella asiatica* extract or *Centella asiatica* meristem cell culture, tetradecyl aminobutyroylvalylamino butyric urea trifluoroacetate, and tripeptide-1 or *Centella asiatica* extract or *Centella asiatica* meristem cell culture, *Alpinia galanga* leaf extract, and tripeptide-1) stimulate proteins that are vital to the health of the DEJ (e.g., collagen, elastin. Fibronectin, and laminin).

An additional embodiment includes an injectably acceptable solution comprising any one of the aforementioned combination of ingredients. An injectably acceptable solution includes a solution that can be safely injected into a human or animal.

One embodiment concerns a method of treating or preventing a disease comprising administering to a person in need thereof any one of the aforementioned combination of ingredients disclosed throughout this specification, wherein the disease is treated or prevented. Non-limiting examples of diseases include AIDS, an autoimmune disease (e.g., rheumatoid arthritis, multiple sclerosis, diabetes—insulin-dependent and non-independent, systemic lupus erythematosus, or Graves disease), a cancer (e.g., malignant, benign, metastatic, or precancer), a cardiovascular disease (e.g., heart disease, or coronary artery disease, stroke—ischemic and hemorrhagic, or rheumatic heart disease), diseases of the nervous system, an infection by a pathogenic microorganism (e.g., Athlete's Foot, Chickenpox, Common cold, Diarrheal diseases, Flu, Genital herpes, Malaria, Meningitis, Pneumonia, Sinusitis, Skin diseases, Strep throat, Tuberculosis, Urinary tract infections, Vaginal infections, or Viral hepatitis), inflammation (e.g., allergy, or asthma), a prion disease (e.g., CJD, kuru, GSS, or FFI), or obesity.

A further embodiment includes a method of treating or preventing hair loss comprising administering to a patient in need thereof a composition comprising any one of the afore mentioned combination of ingredients disclosed throughout this specification. The composition can be included a pharmaceutically (whether topical, oral, injectible, etc.) or dermatologically acceptable vehicle, wherein administering to the patient in need thereof prevents or treats hair loss. Preventing or treating hair loss can include stimulating hair growth on the scalp, in eyebrows, in eyelashes, or on other regions of the body where hair growth is desired. The composition can take the form of an edible pill or gel cap or liquid or powder or foam or spray or aerosolized. The composition can be topically applied, ingested, injected, etc.

The compositions of the present invention can take the form of a pill, gel capsule, spray, foam, topical cream, ointment, gel, or lotion, be aerosolized, or be in powdered form. The compositions can be formulated as emulsions (e.g., oil-in-water, water-in-oil, silicone-in-water, water-in-silicone, water-in-oil-in-water, oil-in-water, oil-in-water-in-oil, oil-in-water-in-silicone, etc.), creams, lotions, solutions (e.g., aqueous or hydro-alcoholic solutions), anhydrous bases (e.g., lipstick or a powder), gels, ointments, milks, pastes, aerosols, solid forms, eye jellies, etc. The compositions can also be formulated for topical skin application at least 1, 2, 3, 4, 5, 6, 7, or more times a day during use. In other aspects of the present invention, compositions can be storage stable or color stable, or both. It is also contemplated that the viscosity of the composition can be selected to achieve a desired result, e.g., depending on the type of composition desired, the viscosity of such composition can be from about 1 cps to well over 1 million cps or any range or integer derivable therein (e.g., 2 cps, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000 cps, etc., as measured on a Brookfield Viscometer using a TC spindle at 2.5 rpm at 25° C.). The compositions of the present invention can include any desired amount of jabotícaba or cashew extract or both. The amount of the extracts can individually or combined be from 0.001, 0.01, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 6, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99%, or more (or any range or integer therein), by weight or volume of the extract or combination of extracts. The compositions in non-limiting aspects can have a pH of about 6 to about 9. In other aspects, the pH can be 1, 2, 3, 4, 5, 6, 7, 8, 9, 10, 11, 12, 13, or 14. The compositions can include a triglyceride. Non-limiting examples include small, medium, and large chain triglycerides. In certain aspects, the triglyceride is a medium chain triglyceride (e.g., caprylic capric triglyceride). The compositions can also include preservatives. Non-limiting examples of preservatives include methylparaben, propylparaben, or a mixture of methylparaben and propylparaben. Compositions of the present invention can have UVA and UVB absorption properties. The compositions can have an sun protection factor (SPF) of 2, 3, 4, 5, 6, 7, 8, 9, 10, 11, 12, 13, 14, 15, 20, 25, 30, 35, 40, 45, 50, 55, 60, or more, or any integer or derivative therein. The compositions can be sunscreen lotions, sprays, or creams.

The compositions of the present invention can also include any one of, any combination of, or all of the following additional ingredients: water, a chelating agent, a moisturizing agent, a preservative, a thickening agent, a silicone containing compound, an essential oil, a structuring agent, a vitamin, a pharmaceutical ingredient, or an antioxidant, or any combination of such ingredients or mixtures of such ingredients. In certain aspects, the composition can include at least two, three, four, five, six, seven, eight, nine, ten, or all of these additional ingredients identified in the previous sentence. Non-limiting examples of these additional ingredients are identified throughout this specification and are incorporated into this section by reference. The amounts of such ingredients can range from 0.0001% to 99.9% by weight or volume of the composition, or any integer or range in between as disclosed in other sections of this specification, which are incorporated into this paragraph by reference.

Also disclosed is a method of lightening skin or evening skin tone comprising applying the compositions of the present invention to the skin. The method can further comprise identify a person in need of lightening skin or evening skin tone. The methods can further include inhibiting melanogenesis in a skin cell, inhibiting tyrosinase or tyrosinase synthesis in a skin cell, or inhibiting melanin transport to keratinocytes in a skin cell. The composition can act as an alpha melanin stimulatory hormone antagonist. The composition can even out pigmentation of the skin. In non-limiting aspect, lightening skin can include reducing the appearance of an age spot, a skin discoloration, a freckle, a sun spot, hyper-pigmented skin, etc., by topical application of the composition to the age spot, a skin discoloration, a freckle, a sun spot, hyper-pigmented skin, etc.

Also disclosed is a method of treating hyperpigmentation comprising applying the compositions of the present invention to the skin. The method can also comprise identifying a person in need of treating hyperpigmentation and applying the composition to a portion of the skin exhibiting hyperpigmentation. Additional methods contemplated by the inventors include methods for reducing the appearance of an age spot, a skin discoloration, or a freckle, reducing or preventing the appearance of fine lines or wrinkles in skin, or increasing the firmness of skin by applying the compositions of the present invention to skin in need of such treatment.

Kits that include the compositions of the present invention are also contemplated. In certain embodiments, the composition is comprised in a container. The container can be a bottle, dispenser, or package. The container can dispense a pre-determined amount of the composition. In certain aspects, the compositions is dispensed in a spray, dollop, or liquid. The container can include indicia on its surface. The indicia can be a word, an abbreviation, a picture, or a symbol.

Also contemplated is a product comprising a composition of the present invention. In non-limiting aspects, the product can be a cosmetic product. The cosmetic product can be those described in other sections of this specification or those known to a person of skill in the art. Non-limiting examples of products include a moisturizer, a cream, a lotion, a skin softener, a foundation, a serum, a cleanser a night cream, a lipstick, a cleanser, a toner, a sunscreen, a mask, an anti-aging product, a deodorant, an antiperspirant, a perfume, a cologne, etc.

It is also contemplated that the compositions disclosed throughout this specification can be used as a leave-on or rinse-off composition. By way of example, a leave-on composition can be one that is topically applied to skin and remains on the skin for a period of time (e.g., at least 5, 6, 7, 8, 9, 10, 20, or 30 minutes, or at least 1, 2, 3, 4, 5, 6, 7, 8, 9, 10, 11, 12, 13, 14, 15, 16, 17, 18, 19, 20, 21, 22, 23 or 24 hours, or over night or throughout the day). Alternatively, a rinse-off composition can be a product that is intended to be applied to the skin and then removed or rinsed from the skin (e.g., with water) within a period of time such as less than 5, 4, 3, 2, or 1 minute. An example of a rinse of composition can be a skin cleanser, shampoo, conditioner, or soap. An example of a leave-on composition can be a skin moisturizer, sunscreen, mask, overnight cream, or a day cream.

It is also contemplated that compositions of the present invention can be included into food-based products (e.g., beverages, fortified water, energy drinks, nutritional drinks, solid foods, vitamins, supplements, etc.) and pharmaceutical products (e.g., pills, injectible solutions, drugs, etc.).

"Supplements" can include vitamins, minerals, herbs or other botanicals, amino acids, enzymes and metabolites. Such supplements are suitable for oral consumption and can be administered orally.

It is contemplated that any embodiment discussed in this specification can be implemented with respect to any method or composition of the invention, and vice versa. Furthermore, compositions of the invention can be used to achieve methods of the invention.

In one embodiment, compositions of the present invention can be pharmaceutically or cosmetically elegant or can have pleasant tactile properties. "Pharmaceutically elegant," "cosmetically elegant," and/or "pleasant tactile properties" describes a composition that has particular tactile properties which feel pleasant on the skin (e.g., compositions that are not too watery or greasy, compositions that have a silky texture, compositions that are non-tacky or sticky, etc.). Pharmaceutically or cosmetically elegant can also relate to the creaminess or lubricity properties of the composition or to the moisture retaining properties of the composition.

"Acne" includes pimples, black heads, white heads, papules, nodules, pustules, inflammatory lesions, or cysts.

"Topical application" means to apply or spread a composition onto the surface of lips or keratinous tissue. "Topical skin composition" includes compositions suitable for topical application on lips or keratinous tissue. Such compositions are typically dermatologically-acceptable in that they do not have undue toxicity, incompatibility, instability, allergic response, and the like, when applied to lips or skin. Topical skin care compositions of the present invention can have a selected viscosity to avoid significant dripping or pooling after application to skin.

"Keratinous tissue" includes keratin-containing layers disposed as the outermost protective covering of mammals and includes, but is not limited to, lips, skin, hair and nails.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The term "substantially" and its variations are defined as being largely but not necessarily wholly what is specified as understood by one of ordinary skill in the art, and in one non-limiting embodiment substantially refers to ranges within 10%, within 5%, within 1%, or within 0.5%.

The terms "inhibiting" or "reducing" or any variation of these terms includes any measurable decrease or complete inhibition to achieve a desired result. The terms "promote" or "increase" or any variation of these terms includes any measurable increase or production of a protein or molecule (e.g., matrix proteins such as fibronectin, laminin, collagen, or elastin or molecules such as hyaluronic acid) to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods for their use can "comprise," "consist essentially of," or "consist of" any of the ingredients or steps disclosed throughout the specification. With respect to the transitional phase "consisting essentially of," in one non-limiting aspect, a basic and novel characteristic of the compositions and methods disclosed in this specification includes the compositions' abilities to reduce the activity of hyaluronidase in skin, promote or increase the production of hyaluronic acid in skin, and/or promote or increase the production of fibronectin and laminin in skin.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

DESCRIPTION OF ILLUSTRATIVE EMBODIMENTS

Figure 1:
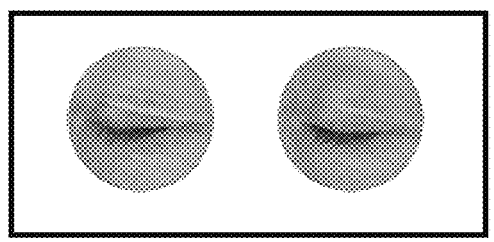
FIG. 1: Before and after picture of skin around the eyes (periorbital region) that has been treated with a combination of *Centella asiatica* stem cells, tetradecyl aminobutyroylvalylamino butyric urea trifluoroacetate, and tripeptide-1.

Skin is in a constant state of degradation and renewal, a process that is kept in optimal balance with younger-aged skin. With age, however, chronological and environmental factors begin to overwhelm the skin, and the dermal matrix begins to degrade faster than it can be renewed, thereby upsetting this delicate balance.

The skin matrix is responsible for structural integrity, mechanical resilience, and stability of the skin. The degradation of the skin matrix plays an important role in the development of wrinkles and other signs of skin aging. Some of the more well-known components of the skin matrix include structural proteins (most notably collagen and elastin), which are vital to skin health and youthfulness. Additional proteins are also critical to the structure and stability of the skin. Laminin and fibronectin are major proteins in the dermal-epidermal junction (DEJ) (also referred to as the basement membrane). The DEJ is located between the dermis and the epidermis interlocks forming fingerlike projections called rete ridges. The cells of the epidermis receive their nutrients from the blood vessels in the dermis. The rete ridges increase the surface area of the epidermis that is exposed to these blood vessels and the needed nutrients. The DEJ provides adhesion of the two tissue compartments and governs the structural integrity of the skin. Laminin and fibronectin are two structural glycoproteins located in the DEJ. Considered the glue that holds the cells together, laminin and fibronectin are secreted by dermal fibroblasts to help facilitate intra- and inter-cellular adhesion of the epidermal calls to the DEJ.

While collagen and elastin fibers provide tensile strength to the skin, they cannot provide the resilience that the tissue needs over time. In addition to the framework of structural proteins, the skin matrix also needs appropriate fillers, which provide mechanical cushioning, hold moisture, and enhance barrier function. The principal skin matrix fillers are glycans, a class of glucose-based polymers which include hyaluronic acid (also referred to as hyaluronan, hyaluronate, or HA). HA is a major component of the extracellular matrix of skin. The larger volume of water hydration associated with HA is a mechanism for maintaining the normal hydration of skin. Further, reduced amounts of HA can bring about the appearance of aged skin at a much more accelerated rate. In this regard, HA has several functions, including binding water to help retain skin moisture, reducing permeability of extracellular fluid, and supporting mechanical resilience and suppleness of the skin. The content of HA within skin decreases with age (after peaking in adolescence or early adulthood). This contributes to the loss of moisture, and the skin becomes thinner and less supple. The loss of HA may also impair the skin's ability to repair itself and possibly affects the synthesis and deposition pattern of other skin matrix components.

In addition to the normal aging process, the amount of HA in skin can also be effected by hyaluronidase, an enzyme that degrades HA. Reducing the activity of HA would effectively increase the overall amount of HA present in skin.

With this backdrop in mind, the inventors discovered a unique combination of ingredients that are not only compatible within one another, but actually work in a synergistic manner in protecting skin matrix proteins and HA within the skin. These combinations of ingredients and other aspects of the present invention are described in non-limiting embodiments in the following subsections.

A. Combination #1

In one instance, the inventors have discovered that a combination of *Centella asiatica* meristem cell culture, tetradecyl aminobutyroylvalylamino butyric urea trifluoroacetate, and tripeptide-1, have the ability to increase synthesis of matrix proteins and contents (e.g., laminin, fibronectin, and hyaluronic acid) of the skin while also reducing the activity of hyaluronidase in skin.

*Centella asiatica* is a small herbaceous annual plant that is native to India, Sri Lanka, northern Australia, Indonesia, and parts of Asia. *Centella asiatica* stem cells are commercially available from Instituto di Ricerche Biotecnologiche (Italy) under the trade name *Centella Asiatic* Stems G™. This product includes glycerin, *Centella asiatica* meristem cell culture, and xanthan gum (INCI name).

Tetradecyl aminobutyroylvalylamino butyric urea trifluoroacetate is a peptide-based ingredient that has the ability to boost hyaluronan production and protect existing collagen in the skin. This ingredient is commercially available from Pentapharm or DSM Nutritional Products AG (Switzerland) under the trade name Syn-Hycan™, which is a mixture of Tetradecyl aminobutyroylvalylamino butyric urea trifluoroacetate, magnesium chloride, and glycerin.

Tripeptide-1 is a synthetic peptide that includes glycine, histidine, and lysine. It has the ability to moisturize skin. This ingredient is commercially available from a wide range of sources (see International Cosmetic Ingredient Dictionary and Handbook, 12$^{th}$ edition, volume 1, pages 458-60 (2008), which is incorporated by reference). In particular instances, the product, Kollaren® (available from Unipex Innovations (Canada), can be used, which is a mixture of water, urea, glucose, guanidine HCL, and tripeptide-1.

B. Combination #2

In another instance, the inventors have discovered that a combination of *Centella asiatica* meristem cell culture, *Alpinia galanga* leaf extract, and tripeptide-1, also have the ability to increase synthesis of matrix proteins and contents (e.g., laminin, fibronectin, and hyaluronic acid) of the skin while also reducing the activity of hyaluronidase in skin.

Descriptions of *Centella asiatica* meristem cell culture and tripeptide-1 are discussed above and incorporated by reference. As for *Alpinia galanga* leaf extract, the plant *Alpinia galanga* is in the ginger family and is native to South Asia and Indonesia. The leaf portion of this plant can be used in the context of the present invention (at the exclusion of other portions of the plant). The extract can be an aqueous extract, a glycolic extract, an alcoholic extract, or any combination thereof. Further the extract is commercially available from BASF (USA) under the trade name HYALU-FIX™ GL, which is a mixture of water, butylene glycol, *Alpinia galanga* leaf extract, xanthan gum, and caprylic/capric triglyceride.

C. Combination #3

In a further instance, the inventors have discovered that a combination of *Centella asiatica* meristem cell culture with tripeptide-1 has the ability to increase synthesis of matrix proteins and contents (e.g., laminin, fibronectin, and hyaluronic acid) of the skin while also reducing the activity of hyaluronidase in skin. These ingredients are described above and incorporated into this section by reference.

D. Additional Combinations

The inventors further discovered additional combinations of ingredients can be added to the above-mentioned ingredients to create multi-purposes cosmetic products. The following additional combinations have been found to be compatible and to work well in cosmetic compositions ranging from eye creams, day creams, night creams, serums, and cleansers.

For instance, a combination that can be used with any one of combinations 1-3 is that of *Myrciaria jaboticaba* extract, *Secale cereale* seed extract, *Spilanthes acmella* flower extract, *Pisum sativum* extract, *Alteromonas* ferment filtrate or extract, and dihydroxymethyl chromone, which can provide additional skin benefits. In particular aspects, this combination of ingredients has been found to work well with skin located on the neck and face. In certain embodiments, a composition having this combination of ingredients is formulated as a serum. *Myrciaria jaboticaba* extract is obtained from the Brazilian Grape Tree, which is a fruit-bearing tree native to Argentina, Brazil and Paraguay. The fruit portion (i.e., *Myrciaria jaboticaba* fruit extract) is particularly useful in the context of the present invention. The fruit has a purplish black skin, with a white pulp. It can be eaten raw or be used to make jellies and plain juice or wine. The inventors discovered that the pulp portion of Jaboticaba has the ability to inhibit both COX-1 and TNF-α in skin cells, while also increasing the synthesis of hyaluronic acid in such cells. Jaboticaba fruit and fruit extract are commercially available from LabCat, the International division of Laboratorio Catarinense (Brazil). Further, a person of ordinary skill in the art would be able to obtain jaboticaba and cashew fruit pulp by mechanical separating the pulp from the other parts of the plants, respectively. As for *Secale cereale* seed extract, it is commercially available from a wide range of sources (see International Cosmetic Ingredient Dictionary and Handbook, 12$^{th}$ edition, volume 2, pages 2452-53 (2008), which is incorporated by reference). In particular instances, the product sold under the trade name Coheliss from Silab (France) is particularly useful with the combinations of the present invention. *Secale cereal* is a grass that is grown worldwide. The seeds of this grass can be used to obtain the extract. With respect to *Spilanthes acmella* flower extract, it too is commercially available from a wide range of sources (see International Cosmetic Ingredient Dictionary and Handbook, 12$^{th}$ edition, volume 2, pages 2633-34 (2008), which is incorporated by reference). *Spilanthes acmella* is a flowering herb that is native to tropical regions of Brazil. Turning to *Pisum sativum* extract, it is commercially available from a wide range of sources (see International Cosmetic Ingredient Dictionary and Handbook, 12$^{th}$ edition, volume 2, page 2042 (2008), which is incorporated by reference). *Alteromonas* ferment filtrate or extract is commercially available from a wide range of sources (see International Cosmetic Ingredient Dictionary and Handbook, 12$^{th}$ edition, volume 1, page 116 (2008), which is incorporated by reference). This ingredient is obtained by fermenting *Alteromonas macleodii*, a deep-sea, mesohphilic, heterotrophic bacterium. In particular aspects, the commercially product Abyssine® sold by Atrium Innovations (France) can be used. Dihydroxymethyl chromone is a chemical compound that can be used as an anti-wrinkle ingredient. The chemical structure of this compound is:

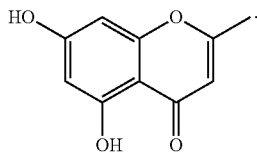

This compound is commercially available from a wide range of sources (e.g., RonaCare® Luremin™, which is sold by EMD Chemicals Inc. (USA)).

Another combination that can be used with any one of combinations 1-3 is *Secale cereale* seed extract, *Alteromonas* ferment filtrate or extract, *Myrciaria jaboticaba* extract, *Argania spinosa* kernel extract, *Asparagopsis armata* extract, *Ascophyllum nodosum* extract, and *Rubus fruticosus* leaf extract. In particular aspects, this combination of ingredients has also been found to work well with skin located on the neck and face. In certain embodiments, a composition having this combination of ingredients is formulated as a serum. *Argania spinosa* kernel extract can be obtained from the kernel of the Argan tree, which is native to the Mediterranean region. This extract is commercially available from a wide range of sources (see International Cosmetic Ingredient Dictionary and Handbook, 12$^{th}$ edition, volume 1, page 198 (2008), which is incorporated by reference). In particular aspects, the product Argatensyl LS™ from Laboratoires Serobiologiques (France) can be used with the combinations of the present invention. *Asparagopsis armata* extract is obtained from red alga and is commercially available from a wide range of sources (see International Cosmetic Ingredient Dictionary and Handbook, 12$^{th}$ edition, volume 1, page 214 (2008), which is incorporated by reference). In particular aspects, the product Aldavine™ sold by Unipex Innovations (Canada) can be used with the combinations of the present invention. Aldavine is a combination of water, *Ascophyllum nodosum* extract, *Asparagopsis armata* extract, and sorbitol. With respect to *Rubus fruticous* leaf extract, it can be obtained by extraction of the leaf of *Rubus fruiticous*, which is a blackberry plant native to the Northern hemisphere and South America. It is commercially available from a wide range of sources (see International Cosmetic Ingredient Dictionary and Handbook, 12$^{th}$ edition, volume 2, page 2399 (2008), which is incorporated by reference).

Another combination that can be used with any one of combinations 1-3 is that of *Magnolia officinalis* bark extract or *Magnolia grandiflora* bark extract, *Magnolia biondii* bud/flower extract, *Brassica campestris* sterols, *Citrus grandis* peel extract, Caprooyl tetrapeptide-3, *Pisum Sativum* extract, Hesperidin methyl chalcone, and Palmitoyl tetrapeptide-7. In particular aspects, this combination of ingredients has also been found to work well with skin located in the periorbital region of the face (e.g., skin around and under the eyes). In certain aspects, this combination can reduce the appearance of dark circles under the eye, puffy skin under the eye, sagging or "bags" under the eye, and increase blood circulation under the eye. In certain embodiments, a composition having this combination of ingredients is formulated as a cream or lotion or emulsion.

A further combination that can be used with any one of combinations 1-3 is that of *Magnolia officinalis* bark extract or *Magnolia grandiflora* bark extract, *Magnolia biondii* bud/flower extract, Hesperidin methyl chalcone, *Pisum sativum* extract, *Citrus grandis* peel extract, Dipeptide-2, Palmitoyl tetrapeptide-7, and Caprooyl tetrapeptide-3. In particular aspects, this combination of ingredients has also been found to work well with skin located in the periorbital region of the face (e.g., skin around and under the eyes). In certain aspects, this combination can reduce the appearance of dark circles under the eye, puffy skin under the eye, sagging or "bags" under the eye, and increase blood circulation under the eye. In certain embodiments, a composition having this combination of ingredients is formulated as a cream or lotion or emulsion.

*Magnolia officinalis* bark extract or *Magnolia grandiflora* bark extract can be obtained from the bark of the *magnolia* tree for the respective species. Similarly, *Magnolia biondii* bud/flower extract is also obtained from the *magnolia* tree. These extracts are commercially available from a wide range of sources (see International Cosmetic Ingredient Dictionary and Handbook, 12$^{th}$ edition, volume 2, pages 1499-50 (2008), which is incorporated by reference). With respect to *Brassica campestris* sterols, this ingredient is commercially available from a wide range of sources (see International Cosmetic Ingredient Dictionary and Handbook, 12$^{th}$ edition, volume 1, page 314 (2008), which is incorporated by reference). This ingredient is a mixture of sterols obtained from *Brassica campestris* (Rapeseed) oil. Turning to *Citrus grandis* peel extract, it is also commercially available from a wide range of sources (see International Cosmetic Ingredient Dictionary and Handbook, 12$^{th}$ edition, volume 1, page 610 (2008), which is incorporated by reference). This extract is obtained from the peel of *Citrus grandis*. Caprooyl tetrapeptide-3 is the reaction product of tetrapeptide-3 (peptide having glycine, histidine, and lysine) and caproic acid. It is commercially available from Unipex Innovations (Canada) under the trade name ChroNOline™, which is a combination of glycerin, water, dextran, and caprooyl tetrapeptide-3. Hesperidin methyl chalcone is a chemical compound that is commercially available from a wide range of sources (see International Cosmetic Ingredient Dictionary and Handbook, 12$^{th}$ edition, volume 1, page 1146 (2008), which is incorporated by reference). In one aspect, this ingredient can be obtained from using Sederama SAS's (France) mixture sold under the trade name Eyeliss™, which is a combination of water, glycerin, hesperidin methyl chalcone, steareth-20, dipeptide-2 (valyl-tryptophane), and palmitoyl tetrapeptide-7 (Pal-GQPR). Palmitoyl tetrapeptide-7, which is the reaction product of palmitic acid and a synthetic peptide containing glycine, glutamine, proline, and arginine), is commercially available from a wide range of sources (see International Cosmetic Ingredient Dictionary and Handbook, 12$^{th}$ edition, volume 2, page 1767 (2008), which is incorporated by reference). In one aspect, this ingredient can be obtained from using Sederama SAS's (France) mixture sold under the trade name Eyeliss™, which is a combination of water, glycerin, hesperidin methyl chalcone, steareth-20, dipeptide-2 (valyl-tryptophane), and palmitoyl tetrapeptide-7 (Pal-GQPR). Dipeptide-2, is a synthetic peptide containing valine and tryptophan. It is commercially available from a wide range of sources (see International Cosmetic Ingredient Dictionary and Handbook, 12$^{th}$ edition, volume 1, page 855 (2008), which is incorporated by reference).

A further combination that can be used with any one of combinations 1-3 is *Silybum marianum* extract or silymarin, 4-t-Butylcyclohexanol, Hexylresorcinol, and *Cestrum latifolium* extract. In certain embodiments, a composition having this combination of ingredients is formulated as a cream or lotion or emulsion. In some instances, the composition can further include *Ascophyllum nodosum* extract and/or *Asparagopsis armata* extract. *Silybum marianum* extract or silymarin, it is commercially available from a wide range of sources (see International Cosmetic Ingredient Dictionary and Handbook, 12$^{th}$ edition, volume 2, page 2478 (2008), which is incorporated by reference). It is obtained from the extraction of lady's thistly, *Silybum marianum*. An active ingredient in the extract is silymarin. In particular aspects, Pronalen Silymarin HSC™ from Provital S.A. (Spain) can be used. With respect to 4-t-Butylcyclohexanol, it is a compound having the following chemical structure:

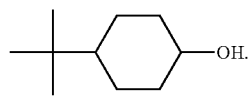

It is commercially available from a wide range of sources (see International Cosmetic Ingredient Dictionary and Handbook, 12$^{th}$ edition, volume 1, page 331 (2008), which is incorporated by reference). Hexylresorcinol is a compound having the following chemical structure:

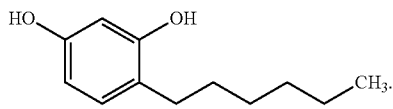 [SMILES: CCCCCCc1ccc(O)cc1O]

It is commercially available from a wide range of sources (see International Cosmetic Ingredient Dictionary and Handbook, 12$^{th}$ edition, volume 1, page 1158 (2008), which is incorporated by reference). As for *Cestrum latifolium* extract, it is obtained from the *Cestrum latifolium* plant, which is native to the tropical regions of the Americas. It is commercially available from BASF Corporation (USA) under the trade name Symbiocell™.

Yet another combination that can be used with any one of combinations 1-3 is that of retinol, *Punica granatum* extract or sterols thereof, *Codium tomentosum* extract, *Cinnamomum Cassia* bark extract, and *Glycyrrhiza glabra* (Licorice) root extract. In certain embodiments, a composition having this combination of ingredients is formulated as a cream or lotion or emulsion. Retinol, a form of vitamin A, has the following chemical structure:

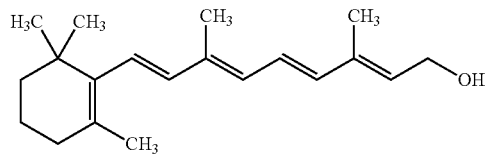 [SMILES: CC1=C(/C=C/C(C)=C/C=C/C(C)=C/CO)C(C)(C)CCC1]

Retinol is commercially available from a wide range of sources (see International Cosmetic Ingredient Dictionary and Handbook, 12$^{th}$ edition, volume 2, page 2363 (2008), which is incorporated by reference). In particular instances, the retinol can be encapsulated by means known in the art or described in this specification. With respect to *Punica granatum* extract or sterols thereof, this ingredient is commercially available from a wide range of sources (see International Cosmetic Ingredient Dictionary and Handbook, 12$^{th}$ edition, volume 2, pages 2315-17 (2008), which is incorporated by reference). In particular instances, *Punica granatum* sterols sold under the trade name ABS Pomegranate Sterols by Active Concepts (USA) can be used. *Codium tomentosum* extract, which is extract from algae, is commercially available from a wide range of sources (see International Cosmetic Ingredient Dictionary and Handbook, 12$^{th}$ edition, volume 1, page 650 (2008), which is incorporated by reference). In particular embodiments, Codiavelane™ from BiotechMarine can be used. *Cinnamomum Cassia* bark extract is obtained via extraction of the bark from *Cinnamomum cassia*. It is commercially available from a wide range of sources (see International Cosmetic Ingredient Dictionary and Handbook, 12$^{th}$ edition, volume 1, page 584 (2008), which is incorporated by reference). *Glycyrrhiza glabra* (Licorice) root extract is obtained via extraction of the root from *Glycyrrhiza glabra*. It is commercially available from a wide range of sources (see International Cosmetic Ingredient Dictionary and Handbook, 12$^{th}$ edition, volume 1, pages 1100-01 (2008), which is incorporated by reference).

Another ingredient that can be used with any one of combinations 1-3 above is Zymo Clear™ MD (mixture of maltodextrin, lipase, and subtilisin). Such a combination has been found to work particularly well in a skin-cleansing base composition. Such a composition can include emulsifiers and/or surfactants but does not require emulsifiers and/or surfactants. Zymo Clear™ MD it is a mixture of maltodextrin, lipase, and subtilisin that is commercially available from Rahn AG (Switzerland).

Another combination that can be used with any one of combinations 1-3 is *Secale cereale* seed extract, *Alteromonas* ferment filtrate or extract, Codium tomentosum extract, *Argania spinosa* kernel extract, *Asparagopsis armata* extract, *Ascophyllum nodosum* extract, and *Rubus fruticosus* leaf extract. In particular aspects, this combination of ingredients has been found to work well with skin located on the neck and face. In certain embodiments, a composition having this combination of ingredients is formulated as a serum.

A further combination that can be used with any one of combinations 1-3 is *Magnolia officinalis* bark extract or *Magnolia grandiflora* bark extract, *Magnolia biondii* bud/ flower extract, hesperidin methyl calcone, *Pisum sativum* extract, *Brassica campostris* sterols, *Citrus grandis* peel extract, dipeptide-2, palmitoyl tetrapeptide-7, and ascorbyl tetraisopalmitate. In further aspects, the combination can further include *Opuntia tuna* fruit extract. In particular aspects, this combination of ingredients has also been found to work well with skin located in the periorbital region of the face (e.g., skin around and under the eyes). In certain aspects, this combination can reduce the appearance of dark circles under the eye, puffy skin under the eye, sagging or "bags" under the eye, and increase blood circulation under the eye. In certain embodiments, a composition having this combination of ingredients is formulated as a cream or lotion or emulsion. Ascorbyl tetraisopalmitate is the tetraester of ascorbic acid and isopalmitic acid. It is commercially available from a wide range of sources (see International Cosmetic Ingredient Dictionary and Handbook, 12$^{th}$ edition, volume 1, pages 212-213 (2008), which is incorporated by reference). As for *Opuntia tuna* fruit extract, it is the extract from the fruit of *Opuntia tuna*. It is commercially available from a wide range of sources (see International Cosmetic Ingredient Dictionary and Handbook, 12$^{th}$ edition, volume 2, page 1731 (2008), which is incorporated by reference).

In still another combination that can be used with any one of combinations 1-3 is retinol, *Punica granatum* extract or sterols thereof, *Codium tomentosum* extract, *Cinnamomum Cassia* bark extract, adenosine, and *Glycyrrhiza glabra* (Licorice) root extract. In certain embodiments, a composition having this combination of ingredients is formulated as a cream or lotion or emulsion. Adenosine is a heterocyclic organic compound generally conforming to the following structure:

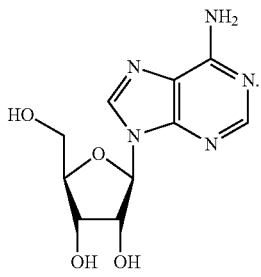

Adenosine is commercially available from a wide range of sources (see International Cosmetic Ingredient Dictionary and Handbook, 12$^{th}$ edition, volume 1, page 60 (2008), which is incorporated by reference).

E. Compositions of the Present Invention

It is contemplated that the compositions of the present invention can include any amount of the ingredients. The compositions can also include any number of combinations of additional ingredients described throughout this specification (e.g., pigments, or additional cosmetic or pharmaceutical ingredients). The concentrations of the any ingredient within the compositions can vary. In non-limiting embodiments, for example, the compositions can comprise, consisting essentially of, or consist of, in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.0550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or any range derivable therein, of at least one of the ingredients that are mentioned throughout the specification and claims. In non-limiting aspects, the percentage can be calculated by weight or volume of the total composition. A person of ordinary skill in the art would understand that the concentrations can vary depending on the addition, substitution, and/or subtraction of ingredients in a given composition.

F. Vehicles

The compositions of the present invention can be incorporated into all types of vehicles. Non-limiting examples include emulsions (e.g., water-in-oil, water-in-oil-in-water, oil-in-water, silicone-in-water, water-in-silicone, oil-in-water-in-oil, oil-in-water-in-silicone emulsions), creams, lotions, solutions (both aqueous and hydro-alcoholic), anhydrous bases (such as lipsticks and powders), gels, and ointments. Variations and other appropriate vehicles will be apparent to the skilled artisan and are appropriate for use in the present invention. In certain aspects, it is important that the concentrations and combinations of the compounds, ingredients, and agents be selected in such a way that the combinations are chemically compatible and do not form complexes which precipitate from the finished product.

G. Cosmetic Products and Articles of Manufacture

The composition of the present invention can also be used in many cosmetic products including, but not limited to, lip sticks, lip balms, lip glosses, sunscreen products, sunless skin tanning products, hair products, finger nail products, moisturizing creams, skin benefit creams and lotions, softeners, day lotions, gels, ointments, foundations, night creams, cleansers, toners, masks, or other known cosmetic products or applications. Additionally, the cosmetic products can be formulated as leave-on or rinse-off products. In certain aspects, the compositions of the present invention are stand-alone products.

H. Additional Ingredients

In addition to the combination of ingredients disclosed by the inventors, the compositions can also include additional ingredients such as cosmetic ingredients and pharmaceutical active ingredients. Non-limiting examples of these additional ingredients are described in the following subsections.

1. Cosmetic Ingredients

The CTFA International Cosmetic Ingredient Dictionary and Handbook (2004 and 2008) describes a wide variety of non-limiting cosmetic ingredients that can be used in the context of the present invention. Examples of these ingredient classes include: fragrances (artificial and natural), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), adsorbents, lubricants, solvents, moisturizers (including, e.g., emollients, humectants, film formers, occlusive agents, and agents that affect the natural moisturization mechanisms of the skin), water-repellants, UV absorbers (physical and chemical absorbers such as paraaminobenzoic acid ("PABA") and corresponding PABA derivatives, titanium dioxide, zinc oxide, etc.), essential oils, vitamins (e.g. A, B, C, D, E, and K), trace metals (e.g. zinc, calcium and selenium), anti-irritants (e.g. steroids and non-steroidal anti-inflammatories), botanical extracts (e.g. *aloe* vera, chamomile, cucumber extract, ginkgo biloba, ginseng, and rosemary), anti-microbial agents, antioxidants (e.g., BHT and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., sorbitol, urea, and manitol), exfoliants, waterproofing agents (e.g., magnesium/aluminum hydroxide stearate), skin conditioning agents (e.g., *aloe* extracts, allantoin, bisabolol, ceramides, dimethicone, hyaluronic acid, and dipotassium glycyrrhizate). Non-limiting examples of some of these ingredients are provided in the following subsections.

a. UV Absorption Agents

UV absorption agents that can be used in combination with the compositions of the present invention include chemical and physical sunblocks. Non-limiting examples of chemical sunblocks that can be used include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (octyl methoxycinnamate, isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate, etc.), anthranilates, ethyl urocanate, homosalate, octisalate, dibenzoylmethane derivatives (e.g., avobenzone), octocrylene, octyl triazone, digalloy trioleate, glyceryl aminobenzoate, lawsone with dihydroxyacetone, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutyiphenol, and bis-ethylhexyloxyphenol methoxyphenyltriazine, 4-methylbenzylidenecamphor, and isopentyl 4-methoxycinnamate. Non-limiting examples of physical sunblocks include, kaolin, talc, petrolatum and metal oxides (e.g., titanium dioxide and zinc oxide).

b. Moisturizing Agents

Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrollidone carboxylic acid, potassium PCA, propylene glycol, sodium glucuronate, sodium PCA, sorbitol, sucrose, trehalose, urea, and xylitol.

Other examples include acetylated lanolin, acetylated lanolin alcohol, alanine, algae extract, *aloe barbadensis*, *aloe-barbadensis* extract, *aloe barbadensis* gel, *althea officinalis* extract, apricot (*prunus armeniaca*) kernel oil, arginine, arginine aspartate, *arnica montana* extract, aspartic acid, avocado (*persea gratissima*) oil, barrier sphingolipids, butyl alcohol, beeswax, behenyl alcohol, beta-sitosterol, birch (*betula alba*) bark extract, borage (*borago officinalis*) extract, butcherbroom (*ruscus aculeatus*) extract, butylene glycol, *calendula officinalis* extract, *calendula officinalis* oil, candelilla (*euphorbia cerifera*) wax, canola oil, caprylic/capric triglyceride, cardamon (*elettaria cardamomum*) oil, carnauba (*copernicia cerifera*) wax, carrot (*daucus carota sativa*) oil, castor (*ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*anthemis nobilis*) oil, cholesterol, cholesterol esters, cholesteryl hydroxystearate, citric acid, clary (*salvia sclarea*) oil, cocoa (*theobroma cacao*) butter, coco-caprylate/caprate, coconut (*cocos nucifera*) oil, collagen, collagen amino acids, corn (*zea mays*) oil, fatty acids, decyl oleate, dimethicone copolyol, dimethiconol, dioctyl adipate, dioctyl succinate, dipentaerythrityl hexacaprylate/hexacaprate, DNA, erythritol, ethoxydiglycol, ethyl linoleate, eucalyptus globulus oil, evening primrose (*oenothera biennis*) oil, fatty acids, geranium maculatum oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*vitis vinifera*) seed oil, hazel (*corylus americana*) nut oil, hazel (*corylus avellana*) nut oil, hexylene glycol, hyaluronic acid, hybrid safflower (*carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*jasminum officinale*) oil, jojoba (*buxus chinensis*) oil, kelp, kukui (*aleurites moluccana*) nut oil, lactamide MEA, laneth-16, laneth-10 acetate, lanolin, lanolin acid, lanolin alcohol, lanolin oil, lanolin wax, lavender (*lavandula angustifolia*) oil, lecithin, lemon (*citrus medica limonum*) oil, linoleic acid, linolenic acid, macadamia ternifolia nut oil, maltitol, matricaria (*chamomilla recutita*) oil, methyl glucose sesquistearate, methylsilanol PCA, mineral oil, mink oil, mortierella oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*olea europaea*) oil, orange (*citrus aurantium dulcis*) oil, palm (*elaeis guineensis*) oil, palmitic acid, pantethine, panthenol, panthenyl ethyl ether, paraffin, PCA, peach (*prunus persica*) kernel oil, peanut (*arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG40 sorbitan peroleate, PEG-5 soy sterol, PEG-10 soy sterol, PEG-2 stearate, PEG-8 stearate, PEG-20 stearate, PEG-32 stearate, PEG40 stearate, PEG-50 stearate, PEG-100 stearate, PEG-150 stearate, pentadecalactone, peppermint (*mentha piperita*) oil, petrolatum, phospholipids, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, retinol, retinyl palmitate, rice (*oryza sativa*) bran oil, RNA, rosemary (*rosmarinus officinalis*) oil, rose oil, safflower (carthamus tinctorius) oil, sage (*salvia officinalis*) oil, sandalwood (*santalum album*) oil, serine, serum protein, sesame (*sesamum indicum*) oil, shea butter (*butyrospermum parkii*), silk powder, sodium chondroitin sulfate, sodium hyaluronate, sodium lactate, sodium palmitate, sodium PCA, sodium polyglutamate, soluble collagen, sorbitan laurate, sorbitan oleate, sorbitan palmitate, sorbitan sesquioleate, sorbitan stearate, sorbitol, soybean (*glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*helianthus annuus*) seed oil, sweet almond (*prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*triticum vulgare*) germ oil, and ylang ylang (*cananga odorata*) oil.

c. Antioxidants

Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCI, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

d. Structuring Agents

In other non-limiting aspects, the compositions of the present invention can include a structuring agent. Structuring agent, in certain aspects, assist in providing rheological characteristics to the composition to contribute to the composition's stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

e. Emulsifiers

In certain aspects of the present invention, the compositions do not include an emulsifier. In other aspects, however, the compositions can include one or more emulsifiers. Emulsifiers can reduce the interfacial tension between phases and improve the formulation and stability of an emulsion. The emulsifiers can be nonionic, cationic, anionic, and zwitterionic emulsifiers (See McCutcheon's (1986); U.S. Pat. Nos. 5,011,681; 4,421,769; 3,755,560). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-100 stearate, and mixtures thereof.

f. Silicone Containing Compounds

In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. In certain aspects, the silicon containing compounds includes a silicone oils such as a polyorganosiloxane. Non-limiting examples of polyorganosiloxanes include dimethicone, cyclomethicone, polysilicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Mich. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Mich.

g. Essential Oils

Essential oils include oils derived from herbs, flowers, trees, and other plants. Such oils are typically present as tiny droplets between the plant's cells, and can be extracted by several method known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160° to 240° C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, macadamia nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the context of the present invention.

h. Thickening Agents

Thickening agents, including thickener or gelling agents, include substances which that can increase the viscosity of a composition. Thickeners includes those that can increase the viscosity of a composition without substantially modifying the efficacy of the active ingredient within the composition. Thickeners can also increase the stability of the compositions of the present invention. In certain aspects of the present invention, thickeners include hydrogenated polyisobutene or trihydroxystearin, or a mixture of both.

Non-limiting examples of additional thickening agents that can be used in the context of the present invention include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid crosslinked with allyl ethers of sucrose or pentaerytritol (e.g., Carbopol™ 900 series from B. F. Goodrich).

Non-limiting examples of crosslinked polyacrylate polymers include cationic and nonionic polymers. Examples are described in U.S. Pat. Nos. 5,100,660; 4,849,484; 4,835,206; 4,628,078; 4,599,379).

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylcelluloses. Other useful polysaccharides include scleroglucans comprising a linear chain of (1-3) linked glucose units with a (1-6) linked glucose every three unit.

Non-limiting examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboyxmethyl dextran, sodium carrageenan, tragacanth gum, xanthan gum, and mixtures thereof.

i. Preservatives

Non-limiting examples of preservatives that can be used in the context of the present invention include quaternary ammonium preservatives such as polyquaternium-1 and benzalkonium halides (e.g., benzalkonium chloride ("BAC") and benzalkonium bromide), parabens (e.g., methylparabens and propylparabens), phenoxyethanol, benzyl alcohol, chlorobutanol, phenol, sorbic acid, thimerosal or combinations thereof.

2. Pharmaceutical Ingredients

Pharmaceutical active agents are also contemplated as being useful with the compositions of the present invention. Non-limiting examples of pharmaceutical active agents include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, antiseborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, wound healing agents, etc.

I. Kits

Kits are also contemplated as being used in certain aspects of the present invention. For instance, compositions of the present invention can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of the composition. In other embodiments, the container can be squeezed (e.g., metal, laminate, or plastic tube) to dispense a desired amount of the composition. The composition can be dispensed as a spray, an aerosol, a liquid, a fluid, or a semi-solid. The containers can have spray, pump, or squeeze mechanisms. A kit can also include instructions for employing the kit components as well the use of any other compositions included in the container. Instructions can include an explanation of how to apply, use, and maintain the compositions.

EXAMPLES

The following examples are included to demonstrate certain non-limiting aspects of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1

Formulations

The Tables 1-2 compositions are non-limiting compositions that can be used in the context of the present invention.

TABLE 1*

| Ingredient | % Concentration (by weight) |
|---|---|
| Phase A | |
| Water | q.s |
| Xanthum gum | 0.1 |
| M-paraben | 0.15 |
| P-paraben | 0.1 |
| Citric acid | 0.01 |
| Phase B | |
| Cetyl alcohol | 4.0 |
| Glyceryl stearate + PEG 100 | 4.0 |
| Octyl palmitate | 4.0 |
| Dimethicone | 1.0 |
| Tocopheryl acetate | 0.2 |
| Phase C | |
| Combination(s)** | 1 to 20 |

*Sprinkle Xanthum gum in water and mix for 10 min. Subsequently, add all ingredients in phase A and heat to 70-75° C. Add all items in phase B to separate beaker and heat to 70-75° C. Mix phases A and B at 70-75° C. Continue mixing and allow composition to cool to 30° C. Subsequently, add phase C ingredient while mixing.
**The combination of ingredients disclosed throughout this specification can be used. For instance, the combination of *Centella asiatica* stem cells, tetradecyl aminobutyroylvalylamino butyric urea trifluoroacetate, and tripeptide-1 can be used. Alternatively, the combination of *Centella asiatica* stem cells, *Alpinia galanga* leaf extract, and tripeptide-1 can be used.

TABLE 2*

| Ingredient | % Concentration (by weight) |
|---|---|
| Phase A | |
| Water | q.s |
| M-paraben | 0.2 |
| P-paraben | 0.1 |
| Na2 EDTA | 0.1 |
| Shea butter | 4.5 |
| Petrolatum | 4.5 |
| Glycerin | 4.0 |
| Propylene Glycol | 2.0 |
| Finsolve TN | 2.0 |
| Phase B | |
| Sepigel 305 | 2.0 |
| Phase C | |
| Combinations(s)** | 1 to 20 |

*Add ingredients in phase A to beaker and heat to 70-75° C. while mixing. Subsequently, add the phase B ingredient with phase A and cool to 30° C. with mixing. Subsequently, add phase C ingredient while mixing.
**The combination of ingredients disclosed throughout this specification can be used. For instance, the combination of *Centella asiatica* stem cells, tetradecyl aminobutyroylvalylamino butyric urea trifluoroacetate, and tripeptide-1 can be used. Alternatively, the combination of *Centella asiatica* stem cells, *Alpinia galanga* leaf extract, and tripeptide-1 can be used.

Example 2

In Vitro Data

Tripeptide-1 (Kollaren from Unipex/Lucas Meyer): Staining of cultured human fibroblasts using immunofluorescent antibodies directed against dermal matrix proteins demonstrate a 305% and 105% increase in collagen I and collagen III, respectively, compared to untreated controls. Additional immunofluorescence studies demonstrate a 15% increase in elastin fibers. Tripeptide-1 was also found to activate the synthesis of laminin and fibronectin by increasing secretion of fibronectin and laminin by 105% and 85%, respectively, compared to untreated controls. Further in vitro studies using cultured human dermal fibroblasts demonstrated that tripeptide-1 also increased the production of hyaluronic acid secretion by 118% compared to an untreated control.

*Centella asiatica* stem cells (*Centella Asiatica* Stems G from Ricerche Biotecnologiche): Enzymatic activity assays demonstrated that stem cells derived from *Centella asiatica* cell cultures (CAS) inhibits the activity of hyaluronidase up to 90% compared to untreated controls.

Tetradecyl aminobutyroylvalylamino butyric urea trifluoroacetate (Syn-Hycan from Pentapharm/DSM): In vitro studies using cultured human dermal fibroblasts demonstrated that tetradecyl aminobutyroylvalylamino butyric urea trifluoroacetate increased the production of hyaluronic acid secretion by 64.2% compared to an untreated control.

The combination of these ingredients were tested in various topical skin formulations (See Example 3) to treat skin. These data suggest a synergistic effect, as each of the ingredients individually are directed to various pathways (e.g, laminin and fibronectin production, inhibition of hyaluronidase, to increased hyaluronic acid production) whereas the combination results in an effective way to improve the appearance aging skin by firming the skin while also adding volume to the skin.

Example 3

In Vivo Data

As noted above, the combination of tripeptide-1 (Kollaren from Unipex/Lucas Meyer), *Centella asiatica* stem cells (*Centella Asiatica* Stems G from Ricerche Biotecnologiche), and tetradecyl aminobutyroylvalylamino butyric urea trifluoroacetate (Syn-Hycan from Pentapharm/DSM) was tested on skin at various levels in various dermatologically acceptable vehicles. The following includes data concerning these tests.

A cleansing formulation having 0.0001% by weight *Centella asiatica* stem cells, 0.00001% by weight tetradecyl aminobutyroylvalylamino butyric urea trifluoroacetate, and 0.000001% by weight of tripeptide-1 was tested by 193 women, using the cleanser twice daily for 1-week. The results of the study were: 86% of the women said the cleanser maintained skin moisture balance; 87% of the women said the cleanser renewed the skin's radiance; 89% of the women said the cleanser left the skin feeling supple; and 90% of the women said the cleanser left the skin feeling pampered.

A serum formulation having 0.25% by weight *Centella asiatica* stem cells, 0.5% by weight tetradecyl aminobutyroylvalylamino butyric urea trifluoroacetate, and 0.5% by weight of tripeptide-1 was tested by 191 women, using the serum twice daily for 4-weeks: 74% of the women said the skin appears tighter; 67% of the women said the youthful volume and vibrancy of the skin are restored; 73% of the women said the serum softens the look of lines and wrinkles on the neck; and 79% of women said that it helped the skin look more youthful all day. After a 12-week clinical study, in which 45 women used the serum twice daily, 89% of the women saw an increase in skin firmness.

A day cream formulation having 0.25% by weight *Centella asiatica* stem cells, 0.5% by weight tetradecyl aminobutyroylvalylamino butyric urea trifluoroacetate, and 0.5% by weight of tripeptide-1 was tested by 181 women, using the cream once a day in the morning for 4-weeks: 70% of the women said the cream minimized the appearance of deep wrinkles; 74% of the women said the cream softened the appearance of crepiness on the neck; 80% of the women said the cream restored youthful cushion to the skin; and 82% of the women said the cream evened the skin tone.

A night cream formulation having 0.05% by weight *Centella asiatica* stem cells, 0.00055% by weight tetradecyl aminobutyroylvalylamino butyric urea trifluoroacetate, and 0.00005% by weight of tripeptide-1 was tested by 185 women, using the cream once a day in the evening for 4-weeks: 76% of the women said the cream improved the advanced signs of aging; 71% of the women said the skin regained firmness; 67% of the women said the jawline area appeared more defined; 81% of the women said the cream restored a youthful cushion to skin; 86% of the women said the cream evened the skin tone; and 90% of the women said that the cream enhanced the skin's overall appearance.

An eye cream formulation having 0.1% by weight *Centella asiatica* stem cells, 0.000001% by weight tetradecyl aminobutyroylvalylamino butyric urea trifluoroacetate, and 0.000055% by weight of tripeptide-1 was tested by 180 women, using the cream twice a day in for 4-weeks: After 1 week of use, 81% of women said the cream reduced the look of crepey skin while 86% of the women said the cream helped minimize the look of under-eye bags and dark circles; after 2 weeks of use, 73% of the women said the cream firmed and toned sagging skin around the eyes, 73% of the women said that the cream minimized the appearance of deep wrinkles, and 71% of the women indicated that the cream restored a youthful lift to the skin; and after 4 weeks of use, 85% of the women said the cream helped repair the skin's appearance while 67% of the women said that the cream reduced the appearance of droopy eyelids. FIG. 1 provides a before and after picture of skin around the eyes after 4 weeks of use, twice daily, of one subject, which illustrates a noticeable decrease in the appearance of wrinkling and crepiness on the upper eyelid and in the crow's feet area.

Figure 2:
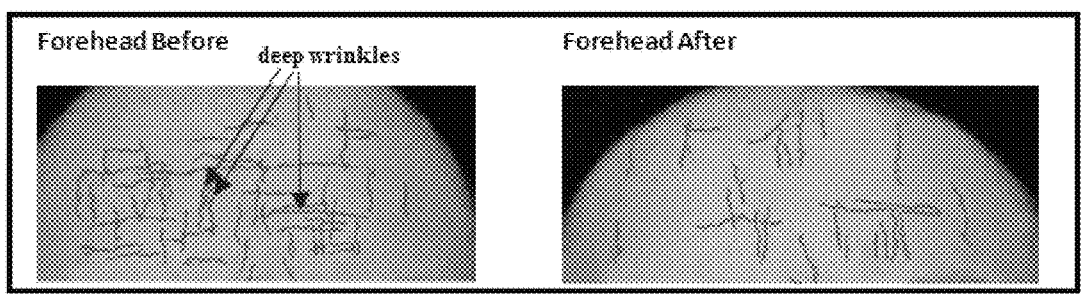
FIG. 2: Before and after picture of skin on an individual's forehead that has been treated with a combination of Before and after picture of skin around the eyes (periorbital region) that has been treated with a combination of *Centella asiatica* stem cells, tetradecyl aminobutyroylvalylamino butyric urea trifluoroacetate, and tripeptide-1. Arrows illustrate deep wrinkles in the before picture, which have disappeared in the after picture. The remaining lines in the before and after pictures represent fine lines in which said lines have been reduced in the after picture.

A regimen using each of the above mentioned formulations daily (as indicated above) for a period of 12 weeks was tested by 43 women. After 12 weeks, 91% of the women indicated that they had less noticeable deep lines and wrinkles, 86% had skin that looked lifted, 98% had less under-eye puffiness, 93% had more even skin tone, and 93% had a significant improvement in overall appearance. Further, 40% of the women observed an improvement in skin firmness and 58% saw an improvement in skin elasticity. Also, 86% of the women had a decrease in the appearance of average wrinkle length, and 81% of the women had a decrease in the appearance of average wrinkle width. Further, 70% of the women showed signs of lifting along the jawline. FIG. 2 provides a before and after picture of skin on an individual's forehead after following the regimen for 12 weeks. This FIG. 2 illustrates a noticeable decrease in the look of deep wrinkles (shown with arrows) and fine lines (remaining lines not highlighted with arrows) across the forehead.

Example 4

In Vitro and Vivo Data

In this study, tetradecyl aminobutyroylvalylamino butyric urea trifluoroacetate (Syn-Hycan from Pentapharm/DSM) was replaced with *Alpinia galanga* leaf extract (Hyalufix™ GL from BASF). Therefore, the combination of tripeptide-1 (Kollaren from Unipex/Lucas Meyer), *Centella asiatica* stem cells (*Centella Asiatica* Stems G from Ricerche Biotecnologiche), and *Alpinia galanga* leaf extract (Hyalufix™ GL from BASF) was tested on skin at various levels in various dermatologically acceptable vehicles. The following includes data concerning these tests. Further, an in vitro assay was performed on *Alpinia galanga* leaf extract using cultured human dermal fibroblasts. This in vitro assay demonstrated the effectiveness of *Alpinia galanga* leaf extract to increase the production of hyaluronic acid in said fibroblasts, while also increasing collagen and laminin production too.

A serum formulation having 0.05% by weight *Centella asiatica* stem cells, 0.025% by weight *Alpinia galanga* leaf extract, and 0.00005% by weight of tripeptide-1 was tested by a population of women, using the serum twice daily for 4-weeks. After 1 week of use, 80% of the women had a noticeable lifting sensation, while 88% had increased skin moisture. After 2 weeks of use, 78% of women said their jawline area appeared lifted, 81% said the serum helped define and perfect facial contours, 82% noticed firmed and tightened skin that was previously sagging, and 79% of women said the serum reversed the loss of cushion in the skin. After 4 weeks, 82% of the women noticed a lifting of the skin that lasts throughout the day, while 79% indicated that the neck area appeared firmed.

An eye cream formulation having 0.002% by weight *Centella asiatica* stem cells and 0.00005% by weight of tripeptide-1 (no *Alpinia galanga* leaf extract was used) was tested by a population of women, using the cream twice daily for 4-weeks. After 1 week of use, 79% of the women said the eye area appeared more lifted, 78% said the under eye puffiness was reduced, and 75% said the crow's feet were minimized. After 2 weeks of use, 83% said dark circles were minimized, 80% said the cream firmed sagging skin around the eyes, and 79% said that the cream minimized the appearance of deep lines. After 4 weeks of use, 81% said that the eyelids had a less hooded appearance, 76% said the eye area appeared dramatically younger, 94% said that the cream helped repair the skin's appearance, and 86% indicated that the skin regained a youthful resilience.

Example 5

Assays

Additional assays that can be used to determine the efficacy of any one of the ingredients or any combination of ingredients or compositions having said combination of ingredients disclosed throughout the specification and claims can be determined by methods known to those of ordinary skill in the art. The following are non-limiting assays that can be used in the context of the present invention. It should be recognized that other testing procedures can be used, including, for example, objective and subjective procedures.

B16 Pigmentation Assay:

Melanogenesis is the process by which melanocytes produce melanin, a naturally produced pigment that imparts color to skin, hair, and eyes. Inhibiting melanogenesis is beneficial to prevent skin darkening and lighten dark spots associated with aging. This bioassay utilizes B16-F1 melanocytes (ATCC), an immortalized mouse melanoma cell line, to analyze the effect of compounds on melanogenesis. The endpoint of this assay is a spectrophotometric measurement of melanin production and cellular viability. B16-F1 melanocytes, can be cultivated in standard DMEM growth medium with 10% fetal bovine serum (Mediatech) at 37° C. in 10% $CO_2$ and then treated with any one of the active ingredients, combination of ingredients, or compositions having said combinations disclosed in the specification for 6 days. Following incubation, melanin secretion was measured by absorbance at 405 nm and cellular viability was quantified.

Collagen Stimulation Assay:

Collagen is an extracellular matrix protein critical for skin structure. Increased synthesis of collagen helps improve skin firmness and elasticity. This bioassay can be used to examine the effect of any one of the active ingredients, combination of ingredients, or compositions having said combinations disclosed in the specification on the production of procollagen peptide (a precursor to collagen) by human epidermal fibroblasts. The endpoint of this assay is a spectrophotometric measurement that reflects the presence of procollagen peptide and cellular viability. The assay employs the quantitative sandwich enzyme immunoassay technique whereby a monoclonal antibody specific for procollagen peptide has been pre-coated onto a microplate. Standards and samples can be pipetted into the wells and any procollagen peptide present is bound by the immobilized antibody. After washing away any unbound substances, an enzyme-linked polyclonal antibody specific for procollagen peptide can be added to the wells. Following a wash to remove any unbound antibody-enzyme reagent, a substrate solution can be added to the wells and color develops in proportion to the amount of procollagen peptide bound in the initial step using a microplate reader for detection at 450 nm. The color development can be stopped and the intensity of the color can be measured. Subconfluent normal human adult epidermal fibroblasts (Cascade Biologics) cultivated in standard DMEM growth medium with 10% fetal bovine serum (Mediatech) at 37° C. in 10% CO2, can be treated with each of the combination of ingredients or compositions having said combinations disclosed in the specification for 3 days. Following incubation, cell culture medium can be collected and the amount of procollagen peptide secretion quantified using a sandwich enzyme linked immuno-sorbant assay (ELISA) from Takara (#MK101).

Tumor Necrosis Factor Alpha (TNF-α) Assay:

The prototype ligand of the TNF superfamily, TNF-α, is a pleiotropic cytokine that plays a central role in inflammation. Increase in its expression is associated with an up regulation in pro-inflammatory activity. This bioassay can be used to analyze the effect of any one of the active ingredients, combination of ingredients, or compositions having said combinations disclosed in the specification on the production of TNF-α by human epidermal keratinocytes. The endpoint of this assay can be a spectrophotometric measurement that reflects the presence of TNF-α and cellular viability. The assay employs the quantitative sandwich enzyme immunoassay technique whereby a monoclonal antibody specific for TNF-α has been pre-coated onto a microplate. Standards and samples can be pipetted into the wells and any TNF-α present is bound by the immobilized antibody. After washing away any unbound substances, an enzyme-linked polyclonal antibody specific for TNF-α can be added to the wells. Following a wash to remove any unbound antibody-enzyme reagent, a substrate solution can be added to the wells and color develops in proportion to the amount of TNF-α bound in the initial step using a microplate reader for detection at 450 nm. The color development can be stopped and the intensity of the color can be measured. Subconfluent normal human adult keratinocytes (Cascade Biologics) cultivated in EpiLife standard growth medium (Cascade Biologics) at 37° C. in 5% $CO_2$, can be treated with phorbol 12-myristate 13-acetate (PMA, 10 ng/ml, Sigma Chemical, #P1585-1MG) and any one of the active ingredients, combination of ingredients, or compositions having said combinations disclosed in the specification for 6 hours. PMA has been shown to cause a dramatic increase in TNF-α secretion which peaks at 6 hours after treatment. Following incubation, cell culture medium can be collected and the amount of TNF-a secretion quantified using a sandwich enzyme linked immuno-sorbant assay (ELISA) from R&D Systems (#DTA00C).

Antioxidant (AO) Assay:

An in vitro bioassay that measures the total anti-oxidant capacity of any one of the ingredients, combination of ingredients, or compositions having said combinations disclosed in the specification. The assay relies on the ability of antioxidants in the sample to inhibit the oxidation of ABTS® (2,2'-azino-di-[3-ethylbenzthiazoline sulphonate]) to ABTS®·+ by metmyoglobin. The antioxidant system of living organisms includes enzymes such as superoxide dismutase, catalase, and glutathione peroxidase; macromolecules such as albumin, ceruloplasmin, and ferritin; and an array of small molecules, including ascorbic acid, α-tocopherol, β-carotene, reduced glutathione, uric acid, and bilirubin. The sum of endogenous and food-derived antioxidants represents the total antioxidant activity of the extracellular fluid. Cooperation of all the different antioxidants provides greater protection against attack by reactive oxygen or nitrogen radicals, than any single compound alone. Thus, the overall antioxidant capacity may give more relevant biological information compared to that obtained by the measurement of individual components, as it considers the cumulative effect of all antioxidants present in plasma and body fluids. The capacity of the antioxidants in the sample to prevent ABTS oxidation is compared with that of Trolox, a water-soluble tocopherol analogue, and is quantified as molar Trolox equivalents. Anti-Oxidant capacity kit #709001 from Cayman Chemical (Ann Arbor, Mich. USA) can be used as an in vitro bioassay to measure the total anti-oxidant capacity of each of any one of the active ingredients, combination of ingredients, or compositions having said combinations disclosed in the specification. The protocol can be followed according to manufacturer recommendations. The assay relied on antioxidants in the sample to inhibit the oxidation of ABTS® (2,2'-azino-di-[3-ethylbenzthiazoline sulphonate]) to ABTS®·+ by metmyoglobin. The capacity of the antioxidants in the sample to prevent ABTS oxidation can be compared with that Trolox, a water-soluble tocopherol analogue, and was quantified as a molar Trolox equivalent.

ORAC Assay:

Oxygen Radical Absorption (or Absorbance) Capacity (ORAC) of any one of the active ingredients, combination of ingredients, or compositions having said combinations disclosed in the specification can also be assayed by measuring the antioxidant activity of such ingredients or compositions. This assay can quantify the degree and length of time it takes to inhibit the action of an oxidizing agent such as oxygen radicals that are known to cause damage cells (e.g., skin cells). The ORAC value of any one of the active ingredients, combination of ingredients, or compositions having said combinations disclosed in the specification can be determined by methods known to those of ordinary skill in the art (see U.S. Publication Nos. 2004/0109905 and 2005/0163880; Cao et al. (1993)), all of which are incorporated by reference). In summary, the assay described in Cao et al. (1993) measures the ability of antioxidant compounds in test materials to inhibit the decline of B-phycoerythrm (B-PE) fluorescence that is induced by a peroxyl radical generator, AAPH.

Mushroom Tyrosinase Activity Assay:

In mammalian cells, tyrosinase catalyzes two steps in the multi-step biosynthesis of melanin pigments from tyrosine (and from the polymerization of dopachrome). Tyrosinase is localized in melanocytes and produces melanin (aromatic quinone compounds) that imparts color to skin, hair, and eyes. Purified mushroom tyrosinase (Sigma) can be incubated with its substrate L-Dopa (Fisher) in the presence or absence of each of the active ingredients, any one of the combination of ingredients, or compositions having said combinations disclosed in the specification. Pigment formation can be evaluated by colorimetric plate reading at 490 nm. The percent inhibition of mushroom tyrosinase activity can be calculated compared to non-treated controls to determine the ability of test ingredients or combinations thereof to inhibit the activity of purified enzyme. Test extract inhibition was compared with that of kojic acid (Sigma).

Matrix Metalloproteinase Enzyme Activity (MMP3; MMP9) Assay:

An in vitro matrix metalloprotease (MMP) inhibition assay. MMPs are extracellular proteases that play a role in many normal and disease states by virtue of their broad substrate specificity. MMP3 substrates include collagens, fibronectins, and laminin; while MMP9 substrates include collagen VII, fibronectins and laminin. Using Colorimetric Drug Discovery kits from BioMol International for MMP3 (AK-400) and MMP-9 (AK-410), this assay is designed to measure protease activity of MMPs using a thiopeptide as a chromogenic substrate (Ac-PLG-[2-mercapto-4-methylpentanoyl]-LG-OC2H5)5,6. The MMP cleavage site peptide bond is replaced by a thioester bond in the thiopeptide. Hydrolysis of this bond by an MMP produces a sulfhydryl group, which reacts with DTNB [5,5'-dithiobis(2-nitrobenzoic acid), Ellman's reagent] to form 2-nitro-5-thiobenzoic acid, which can be detected by its absorbance at 412 nm ($\varepsilon$=13,600 M–1 cm-1 at pH 6.0 and above 7). The active ingredients, any one of the combination of ingredients, or compositions having said combinations disclosed in the specification can be assayed.

Cyclooxygenase (COX) Assay:

An in vitro cyclooxygenase-1 and -2 (COX-1, -2) inhibition assay. COX is a bifunctional enzyme exhibiting both cyclooxygenase and peroxidase activities. The cyclooxygenase activity converts arachidonic acid to a hydroperoxy endoperoxide (Prostaglandin G2; PGG2) and the peroxidase component reduces the endoperoxide (Prostaglandin H2; PGH2) to the corresponding alcohol, the precursor of prostaglandins, thromboxanes, and prostacyclins. This COX Inhibitor screening assay measures the peroxidase component of cyclooxygenases. The peroxidase activity is assayed colorimetrically by monitoring the appearance of oxidized N,N,N',N'-tetramethyl-p-phenylenediamine (TMPD). This inhibitor screening assay includes both COX-1 and COX-2 enzymes in order to screen isozyme-specific inhibitors. The Colormetric COX (ovine) Inhibitor screening assay (#760111, Cayman Chemical) can be used to analyze the effects of each of the active ingredients, any one of the combination of ingredients, or compositions having said combinations disclosed in the specification on the activity of purified cyclooxygnase enzyme (COX-1 or COX-2). According to manufacturer instructions, purified enzyme, heme and test extracts can be mixed in assay buffer and incubated with shaking for 15 min at room temperature. Following incubation, arachidonic acid and colorimetric substrate can be added to initiate the reaction. Color progression can be evaluated by colorimetric plate reading at 590 nm. The percent inhibition of COX-1 or COX-2 activity can be calculated compared to non-treated controls to determine the ability of test extracts to inhibit the activity of purified enzyme.

Lipoxygenase (LO) Assay:

An in vitro lipoxygenase (LO) inhibition assay. LOs are non-heme iron-containing dioxygenases that catalyze the addition of molecular oxygen to fatty acids. Linoleate and arachidonate are the main substrates for LOs in plants and animals. Arachadonic acid may then be converted to hydroxyeicosotrienenoic (HETE) acid derivatives, that are subsequently converted to leukotirenes, potent inflammatory mediators. This assay provides an accurate and convenient method for screening lipoxygenase inhibitors by measuring the hydroperoxides generated from the incubation of a lipoxygenase (5-, 12-, or 15-LO) with arachidonic acid. The Colorimetric LO Inhibitor screening kit (#760700, Cayman Chemical) can be used to determine the ability of each of the active ingredients, any one of the combination of ingredients, or compositions having said combinations disclosed in the specification to inhibit enzyme activity. Purified 15-lipoxygenase and test ingredients can be mixed in assay buffer and incubated with shaking for 10 min at room temperature. Following incubation, arachidonic acid can be added to initiate the reaction and mixtures incubated for an additional 10 min at room temperature. Colorimetric substrate can be added to terminate catalysis and color progression was evaluated by fluorescence plate reading at 490 nm. The percent inhibition of lipoxyganse activity can be calculated compared to non-treated controls to determine the ability of each of the active ingredients, any one of the combination of ingredients, or compositions having said combinations disclosed in the specification to inhibit the activity of purified enzyme.

Elastase Assay:

EnzChek® Elastase Assay (Kit #E-12056) from Molecular Probes (Eugene, Oreg. USA) can be used as an in vitro enzyme inhibition assay for measuring inhibition of elastase activity for each of the active ingredients, any one of the combination of ingredients, or compositions having said combinations disclosed in the specification. The EnzChek kit contains soluble bovine neck ligament elastin that can be labeled with dye such that the conjugate's fluorescence can be quenched. The non-fluorescent substrate can be digested by elastase or other proteases to yield highly fluorescent fragments. The resulting increase in fluorescence can be monitored with a fluorescence microplate reader. Digestion products from the elastin substrate have absorption maxima at ~505 nm and fluorescence emission maxima at ~515 nm. The peptide, chloromethyl ketone, can be used as a selective, collective inhibitor of elastase when utilizing the EnzChek Elastase Assay Kit for screening for elastase inhibitors.

Oil Control Assay:

An assay to measure reduction of sebum secretion from sebaceous glands and/or reduction of sebum production from sebaceous glands can be assayed by using standard techniques known to those having ordinary skill in the art. In one instance, the forehead can be used. Each of the active ingredients, any one of the combination of ingredients, or compositions having said combinations disclosed in the specification can be applied to one portion of the forehead once or twice daily for a set period of days (e.g., 1, 2, 3, 4, 5, 6, 7, 8, 9, 10, 11, 12, 13, 14, or more days), while another portion of the forehead is not treated with the composition. After the set period of days expires, then sebum secretion can be assayed by application of fine blotting paper to the treated and untreated forehead skin. This is done by first removing any sebum from the treated and untreated areas with moist and dry cloths. Blotting paper can then be applied to the treated and untreated areas of the forehead, and an elastic band can be placed around the forehead to gently press the blotting paper onto the skin. After 2 hours the blotting papers can be removed, allowed to dry and then transilluminated. Darker blotting paper correlates with more sebum secretion (or lighter blotting paper correlates with reduced sebum secretion.

Erythema Assay:

An assay to measure the reduction of skin redness can be evaluated using a Minolta Chromometer. Skin erythema may be induced by applying a 0.2% solution of sodium dodecyl sulfate on the forearm of a subject. The area is protected by an occlusive patch for 24 hrs. After 24 hrs, the patch is removed and the irritation-induced redness can be assessed using the a* values of the Minolta Chroma Meter. The a* value measures changes in skin color in the red region. Immediately after reading, the area is treated with the active ingredients, any one of the combination of ingredients, or compositions having said combinations disclosed in the specification. Repeat measurements can be taken at regular intervals to determine the formula's ability to reduce redness and irritation.

Skin Moisture/Hydration Assay:

Skin moisture/hydration benefits can be measured by using impedance measurements with the Nova Dermal Phase Meter. The impedance meter measures changes in skin moisture content. The outer layer of the skin has distinct electrical properties. When skin is dry it conducts electricity very poorly. As it becomes more hydrated increasing conductivity results. Consequently, changes in skin impedance (related to conductivity) can be used to assess changes in skin hydration. The unit can be calibrated according to instrument instructions for each testing day. A notation of temperature and relative humidity can also be made. Subjects can be evaluated as follows: prior to measurement they can equilibrate in a room with defined humidity (e.g., 30-50%) and temperature (e.g., 68-72° C.). Three separate impedance readings can be taken on each side of the face, recorded, and averaged. The T5 setting can be used on the impedance meter which averages the impedance values of every five seconds application to the face. Changes can be reported with statistical variance and significance. Each of the active ingredients, any one of the combination of ingredients, or compositions having said combinations disclosed in the specification can be assayed according to this process.

Skin Clarity and Reduction in Freckles and Age Spots Assay:

Skin clarity and the reduction in freckles and age spots can be evaluated using a Minolta Chromometer. Changes in skin color can be assessed to determine irritation potential due to product treatment using the a* values of the Minolta Chroma Meter. The a* value measures changes in skin color in the red region. This is used to determine whether each of the active ingredients, any one of the combination of ingredients, or compositions having said combinations disclosed in the specification is inducing irritation. The measurements can be made on each side of the face and averaged, as left and right facial values. Skin clarity can also be measured using the Minolta Meter. The measurement is a combination of the a*, b, and L values of the Minolta Meter and is related to skin brightness, and correlates well with skin smoothness and hydration. Skin reading is taken as above. In one non-limiting aspect, skin clarity can be described as L/C where C is chroma and is defined as $(a^2+b^2)^{1/2}$.

Skin Dryness, Surface Fine Lines, Skin Smoothness, and Skin Tone Assay:

Skin dryness, surface fine lines, skin smoothness, and skin tone can be evaluated with clinical grading techniques. For example, clinical grading of skin dryness can be determined by a five point standard Kligman Scale: (0) skin is soft and moist; (1) skin appears normal with no visible dryness; (2) skin feels slightly dry to the touch with no visible flaking; (3) skin feels dry, tough, and has a whitish appearance with some scaling; and (4) skin feels very dry, rough, and has a whitish appearance with scaling. Evaluations can be made independently by two clinicians and averaged.

Clinical Grading of Skin Tone Assay:

Clinical grading of skin tone can be performed via a ten point analog numerical scale: (10) even skin of uniform, pinkish brown color. No dark, erythremic, or scaly patches upon examination with a hand held magnifying lens. Microtexture of the skin very uniform upon touch; (7) even skin tone observed without magnification. No scaly areas, but slight discolorations either due to pigmentation or erythema. No discolorations more than 1 cm in diameter; (4) both skin discoloration and uneven texture easily noticeable. Slight scaliness. Skin rough to the touch in some areas; and (1) uneven skin coloration and texture. Numerous areas of scaliness and discoloration, either hypopigmented, erythremic or dark spots. Large areas of uneven color more than 1 cm in diameter. Evaluations were made independently by two clinicians and averaged.

Clinical Grading of Skin Smoothness Assay:

Clinical grading of skin smoothness can be analyzed via a ten point analog numerical scale: (10) smooth, skin is moist and glistening, no resistance upon dragging finger across surface; (7) somewhat smooth, slight resistance; (4) rough, visibly altered, friction upon rubbing; and (1) rough, flaky, uneven surface. Evaluations were made independently by two clinicians and averaged.

Skin Smoothness and Wrinkle Reduction Assay with Methods Disclosed in Packman et al.

(1978): Skin smoothness and wrinkle reduction can also be assessed visually by using the methods disclosed in Packman et al. (1978). For example, at each subject visit, the depth, shallowness and the total number of superficial facial lines (SFLs) of each subject can be carefully scored and recorded. A numerical score was obtained by multiplying a number factor times a depth/width/length factor. Scores are obtained for the eye area and mouth area (left and right sides) and added together as the total wrinkle score.

Skin Firmness Assay with a Hargens Ballistometer:

Skin firmness can be measured using a Hargens ballistometer, a device that evaluates the elasticity and firmness of the skin by dropping a small body onto the skin and recording its first two rebound peaks. The ballistometry is a small lightweight probe with a relatively blunt tip (4 square mm-contact area) was used. The probe penetrates slightly into the skin and results in measurements that are dependent upon the properties of the outer layers of the skin, including the stratum corneum and outer epidermis and some of the dermal layers.

Skin Softness/Suppleness Assay with a Gas Bearing Electrodynamometer:

Skin softness/suppleness can be evaluated using the Gas Bearing Electrodynamometer, an instrument that measures the stress/strain properties of the skin. The viscoelastic properties of skin correlate with skin moisturization. Measurements can be obtained on the predetermined site on the cheek area by attaching the probe to the skin surface with double-stick tape. A force of approximately 3.5 gm can be applied parallel to the skin surface and the skin displacement is accurately measured. Skin suppleness can then be calculated and is expressed as DSR (Dynamic Spring Rate in gm/mm).

Appearance of Lines and Wrinkles Assay with Replicas:

The appearance of lines and wrinkles on the skin can be evaluated using replicas, which is the impression of the skin's surface. Silicone rubber like material can be used. The replica can be analyzed by image analysis. Changes in the visibility of lines and wrinkles can be objectively quantified via the taking of silicon replicas form the subjects' face and analyzing the replicas image using a computer image analysis system. Replicas can be taken from the eye area and the neck area, and photographed with a digital camera using a low angle incidence lighting. The digital images can be analyzed with an image processing program and are of the replicas covered by wrinkles or fine lines was determined.

Surface Contour of the Skin Assay with a Profilometer/Stylus Method:

The surface contour of the skin can be measured by using the profilometer/Stylus method. This includes either shining a light or dragging a stylus across the replica surface. The vertical displacement of the stylus can be fed into a computer via a distance transducer, and after scanning a fixed length of replica a cross-sectional analysis of skin profile can be generated as a two-dimensional curve. This scan can be repeated any number of times along a fix axis to generate a simulated 3-D picture of the skin. Ten random sections of the replicas using the stylus technique can be obtained and combined to generate average values. The values of interest include Ra which is the arithmetic mean of all roughness (height) values computed by integrating the profile height relative to the mean profile height. Rt which is the maximum vertical distance between the highest peak and lowest trough, and Rz which is the mean peak amplitude minus the mean peak height. Values are given as a calibrated value in mm. Equipment should be standardized prior to each use by scanning metal standards of know values. Ra Value can be computed by the following equation: $R_a$=Standardize roughness; $l_m$=the traverse (scan) length; and y=the absolute value of the location of the profile relative to the mean profile height (x-axis).

MELANODERM™ Assay:

In other non-limiting aspects, the efficacy of each of the active ingredients, any one of the combination of ingredients, or compositions having said combinations disclosed in the specification compositions can be evaluated by using a skin analog, such as, for example, MELANODERM™. Melanocytes, one of the cells in the skin analog, stain positively when exposed to L-dihydroxyphenyl alanine (L-DOPA), a precursor of melanin. The skin analog, MELANODERM™, can be treated with a variety of bases containing each of the active ingredients, any one of the combination of ingredients, or compositions having said combinations disclosed in the specification or with the base alone as a control. Alternatively, an untreated sample of the skin analog can be used as a control.

All of the skin-active ingredients, compositions, or methods disclosed and claimed in this specification can be made and executed without undue experimentation in light of the present disclosure. While the skin-active ingredients, compositions, or methods of this invention have been described in terms of particular embodiments, it will be apparent to those of skill in the art that variations may be applied to the skin-active ingredients, compositions, or methods and in the steps or in the sequence of steps of the method described herein without departing from the concept, spirit and scope of the invention.

The invention claimed is:

1. A method for treating skin, the method comprising topically applying a composition to skin in need of treatment, wherein the composition comprises:
   0.0001-0.3 wt. % of a *Centella asiatica* meristem cell culture to reduce the activity of hyaluronidase in skin;
   0.0001 to 1% by weight of tetradecyl aminobutyroylvalylamino butyric urea trifluoroacetate or 0.0001 to 1% by weight *Alpinia galanga* leaf extract to promote the production of hyaluronic acid in skin;
   0.00001 to 1% by weight of tripeptide-1 to promote the production of fibronectin and laminin in skin;
   retinol;
   *Punica granatum* extract or sterols thereof;
   *Codium tomentosum* extract;
   *Cinnamomum Cassia* bark extract;
   *Glycyrrhiza glabra* (Licorice) root extract; and
   a dermatologically acceptable vehicle,
   wherein topical application of the composition reduces the activity of hyaluronidase in skin, increases the production of hyaluronic acid in skin, and increases the production of fibronectin and laminin in skin.

2. The method of claim 1, wherein the composition includes an effective amount of tetradecyl aminobutyroylvalylamino butyric urea trifluoroacetate to promote the production of hyaluronic acid in skin.

3. The method of claim 1, wherein the composition includes an effective amount of *Alpinia galanga* leaf extract to promote the production of hyaluronic acid in skin.

4. The method of claim 1, wherein the composition further comprises glycerin and xanthan gum.

5. The method of claim 4, wherein the composition comprises tetradecyl aminobutyroylvalylamino butyric urea trifluoroacetate and further comprises magnesium chloride, and water.

6. The method of claim 4, wherein the composition comprises *Alpinia galanga* leaf extract and further comprises water, butylene glycol, and caprylic/capric triglyceride.

7. The method of claim 5, wherein the composition further comprises urea, glucose, and guanidine HCL.

8. The method of claim 6, wherein the composition further comprises urea, glucose, and guanidine HCL.

9. The method of claim 1, wherein the composition is formulated as a serum, cream, or cleanser.

10. The method of claim 1, wherein the composition is applied to a fine line or wrinkle.

11. The method of claim 1, wherein the composition is applied to sagging skin or non-elastic skin.

12. The method of claim 1, wherein the composition is applied to the periorbital region of skin.

13. The method of claim 1, wherein the composition is applied to facial skin or neck skin.

14. The method of claim 1, wherein after topical application the composition remains on the skin for at least 30 minutes.

15. The method of claim 1, wherein the composition further comprises adenosine.

16. The method of claim 1, wherein the dermatologically acceptable vehicle comprises:
   water;
   glycerin;
   *Butyrospermum parkii* (shea) butter;
   glyceryl stearate;
   caprylic/capric triglyceride;
   isocetyl stearate;
   butylene glycol;
   phenoxyethanol;
   PEG-100 stearate;
   dimethicone;
   triethanolamine;
   disodium EDTA; and
   carbomer.

* * * * *